United States Patent [19]

Letton

[11] 4,228,042

[45] Oct. 14, 1980

[54] BIODEGRADABLE CATIONIC SURFACE-ACTIVE AGENTS CONTAINING ESTER OR AMIDE AND POLYALKOXY GROUP

[75] Inventor: James C. Letton, Forest Park, Ohio

[73] Assignee: The Procter & Gamble Company, Cincinnati, Ohio

[21] Appl. No.: 919,343

[22] Filed: Jun. 26, 1978

Related U.S. Application Data

[63] Continuation-in-part of Ser. No. 811,219, Jun. 29, 1977, abandoned.

[51] Int. Cl.[2] .................... C11D 1/62; C11D 1/835; C07C 101/18

[52] U.S. Cl. .................................... 252/528; 282/8.8; 282/547; 260/404; 260/463; 260/561 R; 260/561 A; 260/561 B; 560/179; 560/186; 560/196; 560/155

[58] Field of Search ........................ 252/547, 528, 8.8; 560/196, 60, 155, 179, 186; 260/404, 567.6 M, 567.6 R, 561 A, 561 B, 561 R, 463

[56] References Cited

U.S. PATENT DOCUMENTS

| | | | |
|---|---|---|---|
| 2,176,896 | 10/1939 | Epstein et al. | 260/567.6 M X |
| 2,189,397 | 2/1940 | Harris | 260/404 X |
| 2,189,664 | 2/1940 | Katzman | 252/547 X |
| 2,459,062 | 1/1949 | Cook et al. | 252/547 X |
| 2,950,253 | 8/1960 | Kling et al. | 252/547 X |
| 3,401,119 | 9/1968 | Froehlich | 252/547 X |
| 3,537,993 | 11/1970 | Coward et al. | 252/528 X |
| 3,607,763 | 9/1971 | Salmen et al. | 252/528 |
| 3,959,157 | 5/1976 | Inamorato | 252/547 X |
| 3,983,078 | 9/1976 | Collins | 252/540 |
| 3,989,711 | 11/1976 | Budor | 560/60 X |

FOREIGN PATENT DOCUMENTS 662710 10/1965 Belgium .

*Primary Examiner*—Harris A. Pitlick
*Attorney, Agent, or Firm*—Robert B. Aylor; Thomas H. O'Flaherty; Richard C. Witte

[57] ABSTRACT

Novel, biodegradable cationic surface-active agents are disclosed. These compounds, when used in laundry detergent compositions together with selected nonionic surfactants, provide excellent removal of particulate and greasy/oily soils, as well as providing fabric softening, static control, and dye transfer inhibition benefits to the laundered fabrics.

50 Claims, No Drawings

BIODEGRADABLE CATIONIC SURFACE-ACTIVE AGENTS CONTAINING ESTER OR AMIDE AND POLYALKOXY GROUP

CROSS REFERENCE TO RELATED APPLICATIONS

This application is a continuation-in-part of co-pending application Ser. No. 811,219, Letton, for BIODEGRADABLE CATIONIC SURFACE-ACTIVE AGENTS, filed June 29, 1977, now abandoned.

TECHNICAL FIELD

This invention relates to laundry detergent compositions containing no or low levels of phosphate materials, which exhibit highly improved particulate soil removal capabilities. These detergent compositions provide surprisingly effective clay soil removal performance even in the absence of detergency builders. Similar compositions which utilize mixtures of selected nonionic surfactants and selected cationic surfactants and which give unexpectedly good removal of greasy/oily and body soils are defined in concurrently filed U.S. Patent Application Ser. No. 919,181, Murphy, incorporated herein by reference.

BACKGROUND ART

Nonionic surfactants are generally used in laundry detergent compositions for their ability to remove greasy and oily soils. Cationic surfactants have also been used in detergent compositions, primarily to provide adjunct fabric care benefits, and not for the purpose of cleaning. Certain cationic surfactants have been included in detergent compositions for the purpose of yielding a germicidal or sanitization benefit to washed surfaces; see, for example, U.S. Pat. No. 2,742,434, Kopp, issued Apr. 17, 1956; U.S. Pat. No. 3,539,520, Cantor et al, issued Nov. 10, 1970; and U.S. Pat. No. 3,965,026, Lancz, issued June 22, 1976. Other cationic surfactants, such as ditallowalkyldimethylammonium chloride, are included in detergent compositions for the purpose of yielding a fabric-softening benefit, as disclosed in U.S. Pat. No. 3,607,763, Salmen et al, issued Sept. 21, 1971; and U.S. Pat. No. 3,644,203, Lamberti et al, issued Feb. 22, 1972. Such components are also used to control static, as well as soften laundered fabrics as, for example, in U.S. Pat. No. 3,951,879, Wixon, issued Apr. 20, 1976; and U.S. Pat. No. 3,959,157, Inamorato, issued May 25, 1976. All of the above patents being incorporated herein by reference. However, none of these patents indicate that by the careful selection and combination of certain nonionic and cationic surfactants, to achieve specific nonionic:cationic surfactant ratios and reduced cationic monomer concentrations, outstanding removal of particulate soils may be obtained.

The compositions of the present invention have outstanding cleaning capabilities. In laundry tests, these compositions, not containing any builder components, have been shown to remove clay soils at least as well, and in some cases dramatically better, than fully-built conventional laundry detergent compositions. In addition, the compositions inhibit the transfer of dyes, soften and control static through the washing and drying operations. Further, by selecting the preferred cationic components defined in this application, the compositions additionally provide biodegradability and excellent removal of greasy and oily soils, while also providing, in a single detergent product, particulate soil removal, fabric softening, static control and dye transfer inhibition benefits to the laundered fabrics. The cleaning performance, which is superior to that previously demonstrated, is the result of a heretofore unrecognized cleaning potential of certain selected cationic surfactants when used in the presence of certain selected nonionic surfactants under the conditions specified herein.

It is an object of this invention to provide laundry detergent compositions which yield outstanding particulate soil removal, and which also provide fabric softening, static control and dye transfer inhibition benefits.

It is another object of this invention to provide laundry detergent compositions, yielding excellent particulate soil removal, which may be used in a variety of physical forms, such as liquid, solid, paste, granular, powder, or in conjunction with a carrier such as a substrate.

It is a further more specific object of this invention to provide specific detergent compositions which yield excellent particulate soil removal and which are biodegradable.

It is a still further specific object of this invention to define specific novel cationic surfactants which are biodegradable and which yield excellent particulate and greasy and oily soil removal performance, as well as fabric softening and static control, in the cationic/nonionic surfactant systems of the present invention.

It is another specific object of this invention to provide amide-containing cationic/nonionic surfactant-containing compositions which yield both excellent particulate soil removal and anti-redeposition properties.

It is yet another object of this invention to provide a process for laundering fabrics which yields especially good particulate soil removal, using cationic and nonionic surfactant-containing detergent compositions.

DISCLOSURE OF THE INVENTION

The present invention relates to novel biodegradable cationic surface-active agents, having the formula $$R^3-O[(\overset{R^2}{\overset{|}{C}}H)_nO]_y-(Z^1)_a-(R^4)_t-Z^2-(CH_2)_m-\overset{R^1}{\overset{|}{\underset{\underset{R^1}{|}}{N^+}}}-R^1 \quad X^-$$

wherein each $R^1$ is $C_1$ to $C_4$ alkyl or hydroxyalkyl; each $R^2$ is either hydrogen or $C_1$ to $C_3$ alkyl; $R^3$ is $C_4$ to $C_{30}$ straight or branched chain alkyl, alkenyl or alkylbenzyl; $R^4$ is $C_1$ to $C_{10}$ alkylene or alkenylene; n is from 2 to 4; y is from 1 to 20; a is 0 or 1, and t is 0 or 1, but t must be 1 when a is 1; m is from 1 to 5; $Z^2$ is selected from the group consisting of $$-O-\overset{O}{\overset{\|}{C}}-,\ -\overset{O}{\overset{\|}{C}}-O-,\ -\overset{O}{\overset{\|}{C}}-,\ -O-,\ -O-\overset{O}{\overset{\|}{C}}-O-,$$
$$-\overset{O}{\overset{\|}{C}}-\overset{H}{\overset{|}{N}}-,\ -\overset{H}{\overset{|}{N}}-\overset{O}{\overset{\|}{C}}-,\ -O-\overset{O}{\overset{\|}{C}}-\overset{H}{\overset{|}{N}}-,\ -\overset{H}{\overset{|}{N}}-\overset{O}{\overset{\|}{C}}-O-;$$

$Z^1$ is selected from the group consisting of $$-O-\overset{O}{\overset{\|}{C}}-O-,\ -\overset{O}{\overset{\|}{C}}-,\ -\overset{O}{\overset{\|}{C}}-\overset{H}{\overset{|}{N}}-,\ -\overset{H}{\overset{|}{N}}-\overset{O}{\overset{\|}{C}}-,\ -\overset{H}{\overset{|}{N}}-\overset{O}{\overset{\|}{C}}-O-;$$

and wherein at least one of said $Z^1$ or $Z^2$ is selected from the group consisting of ester, reverse ester, amide, and reverse amide; and X is an anion which makes the surfactant at least water-dispersible.

These compounds, when used in laundry detergent compositions together with selected alcohol polyethoxylate nonionic surfactants, in ratios of nonionic surfactant to cationic surfactant of from about 1:1 to about 100:1, provide excellent removal of both particulate and greasy/oily soils. The compositions also provide fabric care benefits, such as fabric softening, static control, and dye transfter inhibition benefits to fabrics laundered with them.

The compositions of the present invention comprise, by weight, from about 5 to about 100%, particularly from about 10 to about 95%, and most preferably from about 20 to about 90%, of a mixture of the particularly defined cationic and nonionic surfactants in the ratios stated. It is preferred that the detergent compositions contain at least about 1% of the cationic component; otherwise, sufficient cationic surfactant may not be present in the wash solution to provide the desired cleaning results. In addition, preferred compositions contain less than about 10% of the cationic component, due to commercial availability and cost considerations.

The compositions of the present invention may be formulated so as to have a pH of at least about 6 in the laundry solution at conventional usage concentrations in order to optimize cleaning performance; preferably they are alkaline in nature when placed in the laundry solution and have a pH of greater than bout 7. At pH lower than about 6, the particulate soil removal capabilities of the compositions tend to decrease. Particularly preferred compositions have a pH of at least about 8 in the laundry solution, in order to improve the removal of body soil.

The compositions may also be free of oily hydrocarbon materials, such as mineral oil, paraffin oil, dry cleaning solvents and kerosene, because these materials (which are themselves oily in nature), load the washing liquor with excessive oily material, thereby diminishing the cleaning effectiveness of the compositions.

NONIONIC COMPONENT

The nonionic surfactants used in the compositions of the present invention are biodegradable and have the formula $$R(OC_2H_4)_nOH$$

wherein R is a primary or secondary alkyl chain of from about 8 to about 22, preferably from about 10 to 18, carbon atoms and n is an average of from about 2 to about 12, preferably from about 2 to about 9, most preferably from about 2 to about 7, and especially from about 4 to about 7. The nonionic surfactants included within the present invention include branched alcohol ethoxylates. The nonionics have an HLB (hydrophilic-lipophilic balance) of from about 5 to about 17, preferably from about 6 to about 14. Especially useful particulate soil removal can be obtained with nonionic surfactants having HLBs of from about 10 to about 13.5. These nonionic surfactants are preferably combined with less soluble cationic materials (such as those having 2 or 3 long alkyl chains). Where more soluble cationic materials are used, nonionic surfactants of lower HLB may be equally as beneficial. HLB is defined in detail in *Nonionic Surfactants,* by M. J. Schick, Marcel Dekker, Inc., 1966, pp. 607–613, incorporated herein by reference.

Particularly preferred nonionic surfactants for use in the compositions of the present invention include the condensation product of $C_{10}$ alcohol with 3 moles of ethylene oxide, the condensation product of coconut alcohol with 5 moles of ethylene oxide, the condensation product of $C_{12-13}$ alcohol with 6.5 moles of ethylene oxide, the condensation product of $C_{12-13}$ alcohol with 3 moles of ethylene oxide, and the same product which is stripped so as to remove the lower ethoxylate and nonethoxylated fractions, the condensation product of $C_{14-15}$ alcohol with 7 moles of ethylene oxide, the condensation product of $C_{12}$ alcohol with 5 moles of ethylene oxide, the condensation product of $C_{12-13}$ alcohol with 9 moles of ethylene oxide, the condensation product of $C_{14-15}$ alcohol with 3 moles of ethylene oxide, the condensation product of $C_{14-15}$ alcohol with 4 moles of ethylene oxide, and the condensation product of $C_{14-15}$ alcohol with 9 moles of ethylene oxide. A preferred class of such surfactants are made from substantially linear alcohols, such as those which utilize oxoalcohols containing about 20% 2-methyl branched isomers, commercially available under the tradename Neodol, from Shell Chemical Company.

The compositions of the present invention may also contain mixtures of nonionic surfactants falling within the above nonionic surfactant definition, or mixtures of nonionic surfactants, some of which do not fall within the above nonionic surfactant definition, as long as at least one of the nonionic surfactants contained in the mixture falls within the above definition of the nonionic surfactants, and the ratio of that nonionic surfactant to the cationic surfactant falls within the required nonionic/cationic ratio. Where the nonionic surfactant mixture contains a nonionic surfactant (or surfactants) which falls outside of the above nonionic definition, the ratio of the surfactant (or surfactants) within the above definition to that which does not fall within the definition is preferably within the range of from about 1:1 to about 5:1. Specific examples of surfactant mixtures include a mixture of the condensation product of $C_{14-15}$ alcohol with 3 moles of ethylene oxide (Neodol 45-3) and the condensation product of $C_{14-15}$ alcohol with 14 moles of ethylene oxide (Neodol 45-14), in a ratio of lower ethoxylate nonionic to higher ethoxylate nonionic of from about 1:1 to about 3:1; a mixture of the condensation product of $C_{10}$ alcohol with 3 moles of ethylene oxide together with the condensation product of a secondary $C_{15}$ alcohol with 9 moles of ethylene oxide (Tergitol 15-S-9), in a ratio of lower ethoxylate nonionic to higher ethoxylate nonionic of from about 1:1 to about 4:1; and a mixture of Neodol 45-3 and Tergitol 15-S-9, in a ratio of lower ethoxylate nonionic to higher ethoxylate nonionic of from about 1:1 to about 3:1.

Preferred nonionic surfactant mixtures contain alkyl glyceryl ether compounds in addition to the required non-ionic surfactant. Particularly preferred are glyceryl ethers having the formulae

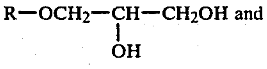
and

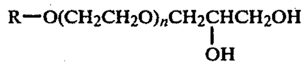

wherein R is an alkyl or alkenyl group of from about 8 to about 18, preferably about 8 to 12 carbon atoms or an alkaryl group having from about 5 to 14 carbons in the alkyl chain, and n is from 1 to about 6, together with the nonionic surfactant component of the present invention, in a ratio of nonionic surfactant to glyceryl ether of from about 1:1 to about 4:1, particularly about 7:3. Glyceryl ethers of the type useful in the present invention are disclosed in U.S. Patent Application Ser. No. 644,214, Jones, filed Dec. 24, 1975, now abandoned and U.S. Patent Application Ser. No. 735,647, Jones, filed Oct. 26, 1976, now U.S. Pat. No. 4,098,713, issued July 4, 1978 both of which are incorporated herein by reference.

Other biodegradable nonionic surfactants well known in the detergency arts may be used, in combination with one or more of the nonionic surfactants falling within the definition of nonionic surfactants required in the present invention, to form useful nonionic surfactant mixtures. Examples of such surfactants are listed in U.S. Pat. No. 3,717,630, Booth, issued Feb. 20, 1973, and U.S. Pat. No. 3,332,880, Kessler et al, issued July 25, 1967, each of which is incorporated herein by reference. Nonlimiting examples of suitable nonionic surfactants which may be used in conjunction with the required nonionic surfactants include the condensation products of aliphatic alcohols with from about 13 to about 25 moles of ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 13 moles of ethylene oxide per mole of alcohol; and the condensation product of about 14 moles of ethylene oxide with coconut alcohol (a mixture of fatty alcohols with alkyl chains varying in length from 10 to 14 carbon atoms).

A preferred group of nonionic surfactants useful herein comprises a mixture of "surfactant" and "cosurfactant", containing at least one nonionic surfactant falling within the definition of nonionic surfactants useful in the present invention, as described in U.S. Patent Application Ser. No. 730,499, Collins, filed Oct. 7, 1976, now abandoned the disclosure of which is incorporated herein by reference.

CATIONIC COMPONENT

The cationic surfactants used in the compositions of the present invention have the formula $$R_m^1R_x^2Y_LZ$$

wherein each $R^1$ is an organic group containing a straight or branched alkyl or alkenyl group optionally substituted with up to three phenyl or hydroxy groups and optionally interrupted by up to four structures selected from the following group:

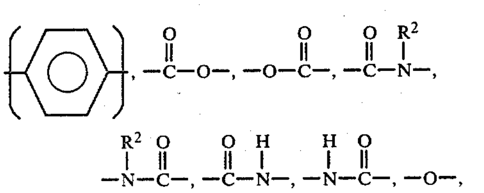

-continued

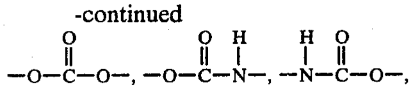

and mixtures thereof, and which contains from about 8 to 22 carbon atoms. The $R^1$ groups may additionally contain up to 12 ethoxy groups. m is a number from 1 to 3. No more than one $R^1$ group in a molecule can have 16 or more carbon atoms when m is 2 or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens. Y is selected from the group consisting of:

(1)
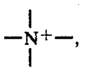

(2)
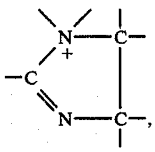

(3)
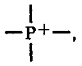

(4)
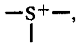

(5)
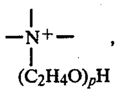
, wherein p is from 1 to 12, (6)
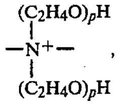
, wherein each p is from 1 to 12, (7)
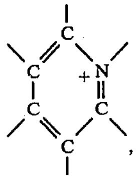

(8)
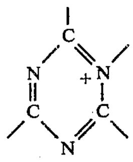
, and mixtures thereof;

(9)

L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water-soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component. The specific cationic component to be included in a given system depends to a large extent upon the particular nonionic component to be included in the system, and is selected such that it is at least water-dispersible, or preferably water-soluble, when mixed with said nonionic surfactant. The term "water-dispersible" means that the cationic and nonionic surfactants, as well as the anions discussed hereinafter, remain dispersed throughout the laundry solution during the washing process. Mixtures of the above-defined cationic materials may also be used in the compositions of the present invention. Small amounts of other cationic materials can be tolerated in such mixtures.

When used in combination with nonionic surfactants, within the specific ratios and the preferred reduced cationic monomer concentrations, defined hereinafter, these cationic components provide excellent soil removal characteristics, confer static control and fabric softening benefits to the laundered fabrics, and inhibit the transfer of certain dyes among the laundered fabrics in the wash solution. Preferred cationic surfactants are those which have critical micelle concentrations less than about 500 ppm.

In preferred cationic materials, L is equal to 1 and Y is

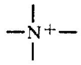
or
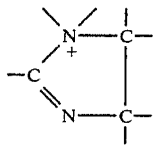

or mixtures thereof. However, L may be 2 and, in that case, the cationic component contains 2 cationic charge centers. Other cationic materials which are useful in the compositions of the present invention include phosphonium and sulfonium materials.

Where m is equal to 1, it is preferred that x is equal to 3 and $R^2$ is a methyl group. Preferred compositions of this mono-long chain type include those in which $R^1$ is a $C_{10}$ to $C_{18}$ alkyl group. Particularly preferred compositions of this class include $C_{12}$ alkyl trimethylammonium halide, $C_{14}$ alkyl trimethylammonium halide, coconutalkyl trimethylammonium halide, tallowalkyl trimethylammonium halide, and $C_{16}$ alkyl trimethylammonium halide.

In order to be sufficiently water-soluble or water-dispersible, the cationic surfactant must satisfy the following chain-length criteria. Where m is equal to 2, only one of the $R^1$ chains can be longer than 16 carbon atoms. Thus, ditallowdimethylammonium chloride and distearyldimethylammonium chloride, which are used conventionally as fabric softeners and static control agents in detergent compositions, are not included within the definition of the cationic components used in the present invention. Preferred di-long chain cationics of this type include those in which x is equal to 2 and $R^2$ is a methyl group. In this instance it is also preferred that $R^1$ is a $C_{10}$ to $C_{14}$ alkyl group. Particularly preferred cationic materials of this class include di-$C_{10}$ alkyldimethylammonium halide, di-$C_{12}$ alkyldimethylammonium halide materials, and dicoconutalkyl dimethylammonium halide.

Where m is equal to 3, only one of the $R^1$ chains can be greater than 12 carbon atoms in length. In this instance, it is preferred that x is equal to 1 and that $R^2$ is a methyl group. In these compositions it is preferred that $R^1$ is a $C_8$ to $C_{12}$ alkyl group. Particularly preferred tri-long chain cationics include trioctylalkylmethylammonium halide, and tridecylalkylmethylammonium halide.

Another type of preferred cationic surfactant for use in the compositions of the present invention are the alkoxylated alkyl quaternaries. Examples of ethoxylated compounds are given below:

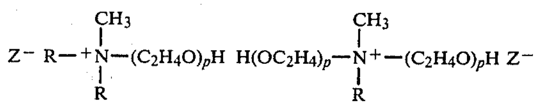

wherein each p is from 1 to 12, preferably from 1 to 10, most preferably from 1 to 7, with the total ethylene oxide groups in a molecule not exceeding about 12. Each R is a $C_{10}$ to $C_{20}$ alkyl group.

The compositions of the present invention are formulated so as to be substantially free of ethoxylated cationic surfactants which contain an average of about 13 or more, and especially more than about 10, moles of ethylene oxide per mole of surfactant. These compounds tend to be relatively nonbiodegradable, do not enhance the cleaning or fabric conditioning benefits provided by the compositions and may, in some circumstances, decrease the overall laundering performance provided by them.

The following formulations have been found to be especially suitable for removing particulate soils, and providing fabric softening, static control and dye transfer inhibition benefits, in a conventional home laundering operation.

(a) Tallowalkyltrimethylammonium halide or methylsulfate, such as chloride, together with a nonionic surfactant selected from the condensation product of $C_{12}$–$C_{13}$ alcohol with 2 to 4 moles of ethylene oxide and the condensation product of $C_{14}$–$C_{15}$ alcohol with 3 to 6 moles of ethylene oxide, such as the condensation product of $C_{12-13}$ alcohol with 3 moles of ethylene oxide, the condensation product of $C_{14-15}$ alcohol with 4 moles of ethylene oxide, or mixtures thereof, in a nonionic:cationic ratio of from 5:1 to about 5:3.

(b) Tallowalkyltrimethylammonium halide or methylsulfate, such as chloride, together with a nonionic surfactant selected from the condensation product of $C_{12}$–$C_{13}$ alcohol with 5 to 7 moles of ethylene oxide and the condensation product of $C_{14}$–$C_{15}$ alcohol with 5 to 8 moles of ethylene oxide, such as the condensation product of $C_{12}$ alcohol with 5 moles of ethylene oxide, the condensation product of $C_{12-13}$ alcohol with 6.5 moles of ethylene oxide, the condensation product of $C_{14-15}$ alcohol with 7 moles of ethylene oxide, or mixtures thereof, in a nonionic:cationic ratio of from 5:1 to about 1:1, especially from 5:1 to about 4:1. Compositions which exhibit both excellent particulate and greasy/oily soil removal may be formulated by combining this cationic material with the condensation product of $C_{12}$–$C_{13}$ alcohol with 4 to 10 moles of ethylene oxide or the condensation product of $C_{14}$–$C_{15}$ alcohol with 6 to 10 moles of ethylene oxide, in nonionic:cationic ratios of from 5:1 to about 1:1.

(c) Coconutalkyltrimethylammonium halide or methylsulfate, such as chloride, together with a nonionic surfactant selected from the condensation product of $C_{12}$–$C_{13}$ alcohol with 2 to 4 moles of ethylene oxide and the condensation product of $C_{14}$–$C_{15}$ alcohol with 3 to 6 moles of ethylene oxide, such as the condensation product of $C_{12-13}$ alcohol with 3 moles of ethylene oxide, the condensation product of $C_{14-15}$ alcohol with 4 moles of ethylene oxide, or mixtures thereof in a nonionic:cationic ratio of from 5:1 to about 1:1.

(d) Coconutalkyltrimethylammonium halide or methylsulfate, such as chloride, together with a nonionic surfactant selected from the condensation product of $C_{12}$–$C_{13}$ alcohol with 5 to 7 moles of ethylene oxide and the condensation product of $C_{14}$–$C_{15}$ alcohol with 5 to 8 moles of ethylene oxide, such as the condensation product of the condensation product of $C_{12}$ alcohol with 5 moles of ethylene oxide, the condensation product of $C_{12-13}$ alcohol with 6.5 moles of ethylene oxide, the condensation product of $C_{14-15}$ alcohol with 7 moles of ethylene oxide, or mixtures thereof, in a nonionic:cationic ratio of from 5:1 to about 1:1, especially about 3:1. Compositions which exhibit both excellent particulate and greasy/oily soil removal may be formulated by combining this cationic material with the condensation product of $C_{12}$–$C_{13}$ alcohol with 4 to 10 moles of ethylene oxide or the condensation product of $C_{14}$–$C_{15}$ alcohol with 6 to 10 moles of ethylene oxide, in nonionic: cationic ratios of from 5:1 to about 1:1.

(e) A cationic surfactant of the formula

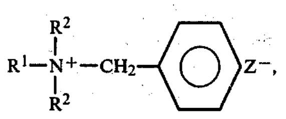

wherein $R^1$, $R^2$ and Z are as defined above, together with a nonionic surfactant selected from the condensation products of $C_{12}$–$C_{15}$ alcohols with 2 to 4 moles of ethylene oxide, such as the condensation product of $C_{12-13}$ alcohol with 3 moles of ethylene oxide, the condensation product of $C_{14-15}$ alcohol with 4 moles of ethylene oxide, or mixtures thereof, in a nonionic:cationic ratio of from about 3:1 to about 1:1.

(f) A cationic surfactant of the formula

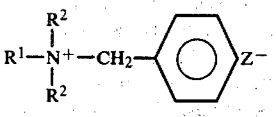

wherein $R^1$, $R^2$ and Z are as defined above, together with a nonionic surfactant selected from the condensation products of $C_{12}$–$C_{15}$ alcohols with 5 to 10 moles of ethylene oxide, such as the condensation product of $C_{12}$ alcohol with 5 moles of ethylene oxide, the condensation product of $C_{12-13}$ alcohol with 6.5 moles of ethylene oxide, the condensation product of $C_{14-15}$ alcohol with 7 moles of ethylene oxide, or mixtures thereof, in a nonionic:cationic ratio of from 5:1 to about 1:1.

(g) Dicoconutalkyldimethylammonium halide, or methylsulfate such as chloride, together with a nonionic surfactant selected from the condensation product of $C_{12}$–$C_{13}$ alcohol with 4 to 8 moles of ethylene oxide or the condensation product of $C_{14}$–$C_{15}$ alcohol with 4 to 8 moles of ethylene oxide, such as the condensation product of $C_{12}$ alcohol with 5 moles of ethylene oxide, the condensation product of $C_{12-13}$ alcohol with 6.5 moles of ethylene oxide, the condensation product of $C_{14-15}$ alcohol with 7 moles of ethylene oxide, or mixtures thereof, in a nonionic:cationic ratio of from 5:1 to about 1:1, especially from about 4:1 to about 2:1. Compositions which give both excellent particulate and greasy/oily soil removal can be obtained by combining this cationic surfactant with the condensation product of $C_{12}$–$C_{13}$ alcohol with 6 to 10 moles of ethylene oxide in nonionic:cationic ratios of from 5:1 to about 4:1.

(h) Tri-$C_{12}$alkylmethylammonium halide or methylsulfate, such as chloride, together with a nonionic surfactant selected from the condensation product of $C_{12}$–$C_{13}$ alcohol with 6 to 10 moles of ethylene oxide and the condensation product of $C_{14}$–$C_{15}$ alcohol with 6 to 10 moles of ethylene oxide, such as the condensation product of $C_{12-13}$ alcohol with 6.5 moles of ethylene oxide, the condensation product of $C_{12-13}$ alcohol with 9 moles of ethylene oxide, the condensation product of $C_{14-15}$ alcohol with 7 moles of ethylene oxide, the condensation product of $C_{14-15}$ alcohol with 9 moles of ethylene oxide, or mixtures thereof, in a nonionic:cationic ratio of from 5:1 to about 1:1, especially from 5:1 to about 5:3.

(i) Tri-$C_{8-10}$alkylmethylammonium halide or methylsulfate, such as chloride, together with nonionic surfactant selected from the condensation product of $C_{12}$–$C_{13}$ alcohol with 5 to 10 moles of ethylene oxide, and the condensation product of $C_{14}$–$C_{15}$ alcohol with 6 to 10 moles of ethylene oxide, such as the condensation product of $C_{12}$ alcohol with 5 moles of ethylene oxide, the condensation product of $C_{12-13}$ alcohol with 6.5 moles of ethylene oxide, the condensation product of $C_{12-13}$ alcohol with 9 moles of ethylene oxide, the condensation product of $C_{14-15}$ alcohol with 7 moles of ethylene oxide, the condensation product of $C_{14-15}$ alcohol with 9 moles of ethylene oxide, or mixtures thereof, in a nonionic:cationic ratio of from about 3:1 to about 1:1.

A particularly preferred type of cationic component, which is described in U.S. Patent Application Ser. No. 919,344, Letton, filed of even date, and incorporated herein by reference, and which is a continuation-in-part of U.S. Patent Application Ser. No. 811,218, filed June 29, 1977, now abandoned has the formula

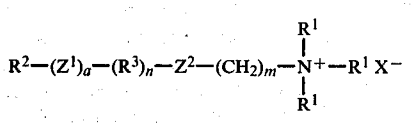

wherein $R^1$ is $C_1$ to $C_4$ alkyl or hydroxyalkyl; $R^2$ is $C_5$ to $C_{30}$ straight or branched chain alkyl or alkenyl, alkyl phenyl, or

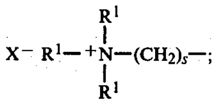

wherein s is from 0 to 5; $R^3$ is $C_1$ to $C_{20}$ alkylene or alkenylene; a is 0 or 1, n is 0 or 1, and n is 1 when a is 1; m is from 1 to 5; $Z^1$ and $Z^2$ are each selected from the group consisting of

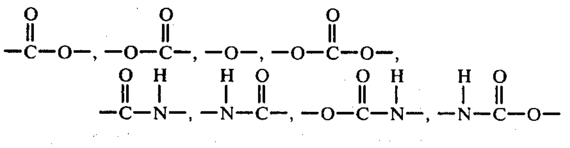

and wherein at least one of said groups is an ester, reverse ester, amide or reverse amide; and X is an anion which makes the compound at least water-dispersible, preferably selected from the group consisting of halide, methyl sulfate, and nitrate, preferably chloride, bromide, iodide, sulfate, or methyl sulfate.

In addition to the advantages of the other cationic surfactants disclosed herein, this particular cationic component is environmentally desirable, since it is biodegradable, yielding environmentally acceptable compounds, both in terms of its long alkyl fragment and its nitrogen-containing fragment. These preferred cationic components are useful in nonionic/cationic surfactant mixtures which have a ratio of nonionic to cationic of from about 1:1 to about 100:1. However, when used in the compositions of the present invention, they are used in surfactant mixtures which have nonionic to cationic ratios of from 5:1 to about 1:1, more preferably from 5:1 to about 5:3, particularly from about 10:3 to about 10:5, most preferably about 10:4. In preferred compositions, the ratios are selected such that the compositions have reduced cationic monomer concentrations as specified herein. These preferred cationic surfactants may also be used in the detergent systems defined in U.S. Patent Application Ser. No. 919,181, Murphy, filed of even date, incorporated herein by reference, in nonionic to cationic ratios of 5.1:1 to about 100:1, preferably from 5.1 to about 50:1, particularly from about 6:1 to about 40:1, and most particularly from about 6:1 to about 20:1. In formulating such compositions, the nonionic/cationic surfactant mixture should have a cloud point of from about 0° to about 95° C., preferably from about 10° to about 70° C., most preferably from about 20° to about 70° C., and in preferred compositions, the surfactant mixture has a reduced cationic monomer concentration of from about 0.002 to about 0.2, especially from about 0.002 to about 0.15, particularly from about 0.002 to about 0.08.

Where this type of biodegradable cationic surfactant is used, it is preferred that the detergent compositions have a pH of not greater than about 11, preferably less than about 10, in the laundry solution, in order to minimize hydrolysis of the cationic surfactant.

Particularly preferred cationic surfactants of this type are the choline ester derivatives having the following formula:

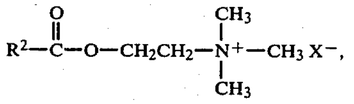

as well as those wherein the ester linkage in the above formula is replaced with a reverse ester, amide or reverse amide linkage.

Particularly preferred examples of this type of cationic surfactant include stearoyl choline ester quaternary ammonium halides ($R^2=C_{17}$ alkyl), palmitoyl choline ester quaternary ammonium halides ($R^2=C_{15}$ alkyl), myristoyl choline ester quaternary ammonium halides ($R^2=C_{13}$ alkyl), lauroyl choline ester ammonium halides ($R^2=C_{11}$ alkyl), and tallowyl choline ester quaternary ammonium halides ($R^2=C_{15}$-$C_{17}$ alkyl).

Additional preferred cationic components of the choline ester variety are given by the structural formulas below, wherein p may be from 0 to 20.

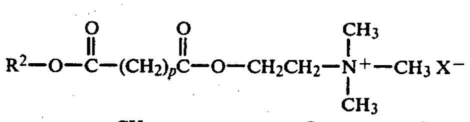

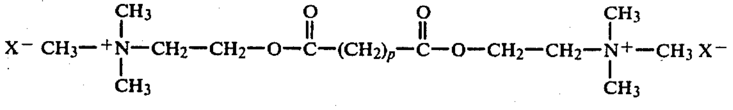

The preferred choline-derivative cationic substances, discussed above, may be prepared by the direct esterification of a fatty acid of the desired chain length with dimethylaminoethanol, in the presence of an acid catalyst. The reaction product is then quaternized with a methyl halide, forming the desired cationic material. The choline-derived cationic materials may also be prepared by the direct esterification of a long chain fatty acid of the desired chain length together with 2-haloethanol, in the presence of an acid catalyst material. The reaction product is then used to quaternize trimethylamine, forming the desired cationic component.

The novel, particularly preferred cationic materials of the present invention have the formula

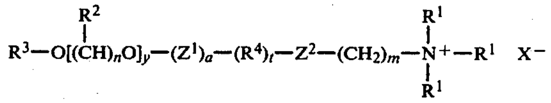

In the formula, each $R^1$ is a $C_1$ to $C_4$ alkyl or hydroxyalkyl group, preferably a methyl group. Each $R^2$ is either hydrogen or $C_1$ to $C_3$ alkyl, preferably hydrogen. $R^3$ is a $C_4$ to $C_{30}$ straight or branched chain alkyl, alkenyl, alkyl phenyl, or alkyl benzyl group, preferably a $C_8$ to $C_{18}$ alkyl group, most preferably a $C_{12}$ alkyl group. $R^4$ is a $C_1$ to $C_{10}$ alkylene or alkenylene group. n is from 2 to 4, preferably 2; y is from 1 to 20, preferably from about 1 to 10, most preferably about 7; a may be 0 or 1, and t may be 0 or 1, but t must be 1 when a is 1; and m is from 1 to 5, preferably 2. $Z^2$ is selected from the group consisting of:

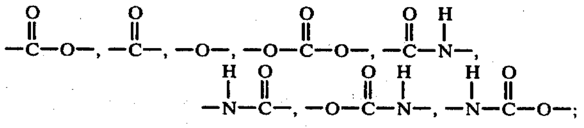

$Z^1$ is selected from the group consisting of:

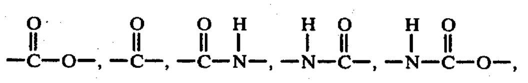

and wherein at least one of said $Z^1$ and $Z^2$ groups is selected from the group consisting of ester, reverse ester, amide and reverse amide. X is an anion which will make the compound at least water-dispersible, and is selected from the group consisting of halides, methyl sulfate, and nitrate, particularly chloride, bromide, iodide, sulfate, and methyl sulfate. Mixtures of the above structures can also be used.

These novel cationic surfactants may be used in nonionic/cationic surfactant mixtures in a ratio of nonionic component to cationic component of from about 1:1 to about 100:1. When these surfactants are used in the compositions of the present invention they are used in nonionic to cationic ratios of from 5:1 to about 1:1, more preferably from 5:1 to about 5:3, particularly from about 10:3 to about 10:5, especially about 10:4, and preferably have ratios which yield reduced cationic monomer concentrations within the range given herein. They may be also used in the nonionic/cationic surfactant mixtures disclosed in U.S. Application Ser. No. 919,181, Murphy, filed of even date, wherein the ratio of nonionic component to cationic component would be from 5.1:1 to about 100:1, preferably from 5.1:1 to about 50:1, particularly from about 6:1 to about 40:1, and most particularly from about 6:1 to about 20:1. In formulating such compositions, the nonionic/cationic surfactant mixture should have a cloud point of from about 0° to about 95° C., preferably from about 10° to about 70° C., most preferably from about 20° to about 70° C., and the surfactant mixture preferably has a reduced cationic monomer concentration of from about 0.002 to about 0.2, especially from about 0.002 to about 0.15, particularly from about 0.002 to about 0.08.

These surfactants, when used in the compositions of the present invention, yield excellent particulate soil, body soil, and grease and oil soil removal. In addition, the detergent compositions control static and soften the fabrics laundered therewith, and inhibit the transfer of certain dyes in the washing solution. Further, these novel cationic surfactants are environmentally desirable, since both their long chain alkyl fragments and their nitrogen fragments are biodegradable, in that they degrade to yield environmentally acceptable compounds. Where this type of biodegradable cationic surfactant is used, it is preferred that the detergent compositions have a pH of not greater than about 11, preferably less than about 10, in the laundry solution, in order to minimize hydrolysis of the cationic surfactant.

Preferred embodiments of this type of cationic component are the esters in which $R^1$ is a methyl group and $Z^2$ is an ester or reverse ester group, particular formulas of which are given below, in which t is 0 or 1 and y is from 1 to 20.

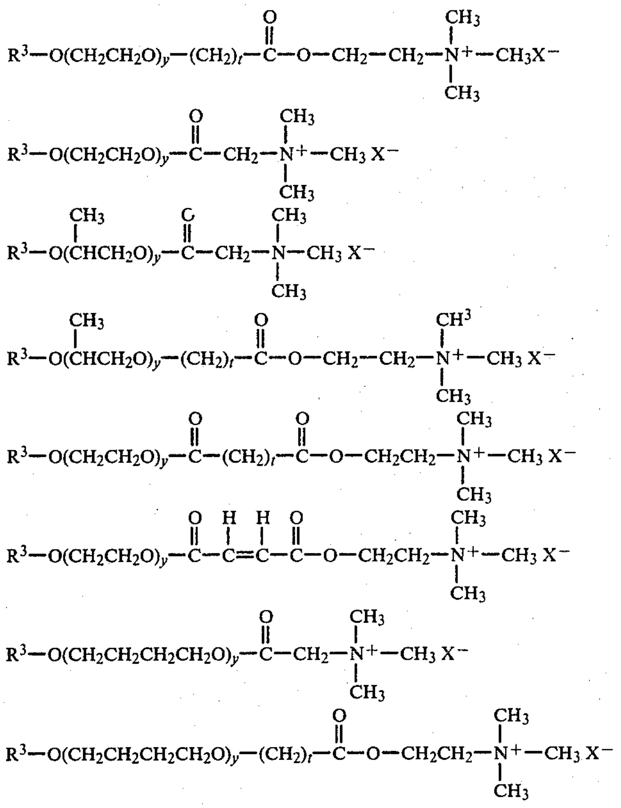

The preferred derivatives, described above, may be prepared by the reaction of a long chain alkyl polyalkoxy (preferably polyethoxy) carboxylate, having an alkyl chain of desired length, with oxalyl chloride, to form the corresponding acid chloride. The acid chloride is then reacted with dimethylaminoethanol to form the appropriate amine ester, which is then quaternized with a methyl halide to form the desired choline ester compound. Another way of preparing these compounds is by the direct esterification of the appropriate long chain ethoxylated carboxylic acid together with 2-haloethanol or dimethyl aminoethanol, in the presence of heat and an acid catalyst. The reaction product formed is then quaternized with methylhalide or used to quaternize trimethylamine to form the desired choline ester compound.

As a guide in formulating compositions which deliver excellent particulate soil removal, the reduced cationic monomer concentration may be used. Thus, the nonionic and cationic components, defined above, may be combined into a surfactant mixture which has a ratio corresponding to a reduced cationic monomer concentration ($C_R$) of from about 0.005 to about 0.2, preferably from about 0.008 to about 0.15, particularly from about 0.01 to about 0.1. A $C_R$ value within this range will yield a composition which exhibits optimum particulate soil removal performance. Where the nonionic and cationic components used are pure, the more narrow $C_R$ ranges are preferred. In a preferred method of preparing the compositions of the present invention, the nonionic and cationic surfactants are intimately and completely mixed together prior to the addition of any additional components to the mixture. This intimate premixing of the nonionic and cationic components enhances performance of the compositions.

An approximation of the $C_R$ of a surfactant mixture is obtained by dividing the concentration of the cationic surfactant monomer in the laundry solution by the critical micelle concentration (CMC) of the surfactant. As used in this application, CMC's are determined at 105° F. in water containing 7 grains/gallon of mixed hardness, unless otherwise stated. For purposes of this application, $C_R$ is calculated according to the equations given below.

The concept of reduced monomer concentration is derived from the discussion in Tamamushi and Tamaki, *Proceedings of the Second International Congress of Surface Activity,* III, 449, Academic Press, Inc. (1957), and in Clint, *J. Chem. Soc. Far. Trans.,* I, 71, 1327 (1975), incorporated herein by reference, in the context of an ideal solution, and is based on the following quadratic equation (equation (11) in Clint):

$$(c_1^m)^2\left[\frac{c_2^*}{c_1^*} - 1\right] + c_1^m(C - c_2^* + c_1^*) - \alpha C c_1^* = 0$$

wherein in the above and the following equations:

- C=total analytical surfactant concentration in the solution (moles/l.)=sum of the cationic and nonionic concentrations=$C_1+C_2$ (wherein "1" denotes nonionic surfactant and "2" denotes cationic surfactant)
- $c_1^*$=critical micelle concentration (CMC) of nonionic surfactant (moles/l.)
- $c_2^*$=critical micelle concentration of cationic surfactant (moles/l.)
- $\alpha$=total mole fraction of nonionic surfactant in the solution=$C_1/(C_1+C_2)$
- $\beta$=a constant based upon the heat of mixing=$-2.8$
- $c_1^m$=nonionic monomer concentration
- $c_2^m$=cationic monomer concentration
- e=base of Napierian logarithm system=$2.7\overline{1828}$
- x=mole fraction of the nonionic surfactant in the micelle at concentration C
- $f_1$=nonionic activity coefficient in the mixed micelle=$e^{\beta(1-x)^2}$
- $f_2$=cationic activity coefficient in the mixed micelle=$e^{\beta x^2}$
- $\Delta = f_2c_2^* - f_1c_1^*$
- $C_R$=reduced cationic monomer concentration
- $M_1$=molecular weight of nonionic surfactant
- $M_2$=molecular weight of cationic surfactant
- W=total analytical surfactant concentration in the solution (ppm)=sum of the cationic and nonionic concentrations (ppm)=$W_1+W_2$ (wherein "1" denotes nonionic surfactant and "2" denotes cationic surfactant)
- Y=weight fraction of nonionic surfactant in the composition The above equation is solved for the nonionic monomer concentration by taking its positive root (equation (12) in Clint).

$$c_1^m = \frac{\{-(C - (c^* - c_1^*)) \pm [(C - (c_2^* - c_1^*))^2 + 4\alpha C(c_2^* - c_1^*)]^{\frac{1}{2}}\}}{2\left(\frac{c_2^*}{c_1^*} - 1\right)}$$

By modifying this equation based on the assumptions of a regular, rather than an ideal, solution, the $C_R$ range for optimum performance was derived from the following equation:

$$x = \frac{-(C - \Delta) + \sqrt{(C - \Delta)^2 + 4\alpha C\Delta}}{2\Delta} \quad (1)$$

For a given cleaning test for a nonionic/cationic system, x was found by inserting the values known from the test (i.e., $c_1^*$, $c_2^*$, $\alpha$, C and $\beta$) into equation (1) and solving iteratively for x, such that the error in x is less than 0.001. This procedure was repeated for a large number of such tests, over varying usage conditions. The x values obtained were then used to solve for the cationic monomer concentrations using the following equation:

$$c_2^m = (1-x)f_2c_2^* \quad (2)$$

The $C_R$ value was then calculated using equation (3).

$$C_R = c_2^m/c_2^* \quad (3)$$

The $C_R$ values obtained cover a large number of combinations and ratios of various nonionic and cationic surfactants, at various concentrations and temperatures, which have been evaluated for their ability to clean greasy/oily soils. The examination of the resulting data revealed that for a given system the optimum cleaning of greasy/oily soils was found at a $C_R$ value of from about 0.002 to about 0.2.

This range of $C_R$ (i.e., 0.002 to 0.2) can then be used to determine the range of optimum nonionic/cationic ratios for any given combination of nonionic surfactant and cationic surfactant, for the desired wash concentration within the overall wash concentration range of from 100 parts per million (ppm) to 10,000 ppm of surfactant. This calculation is carried out in the following manner, where $\beta$, $C_R$, $c_1^*$, $c_2^*$, $M_1$ and $M_2$ are known for a given nonionic/cationic surfactant pair:

(a) for a given nonionic surfactant, cationic surfactant, and for each end of the $C_R$ range, solve for x using the equation $$(1-x)e^{\beta x^2} = C_R$$

by standard numerical iterative techniques to an error in x of less than 0.001;

(b) find the range of Y from the equation $$Y(1-x)/M_1 - x(1-Y)/M_2 = 1000/W\,[x(x-1)\Delta]$$

using 100 ppm and 10,000 ppm as the boundary values for W, for each end of the $C_R$ range;

(c) the nonionic/cationic ratio (NCR) range for optimum performance is then within the range obtained by substituting the boundary values for Y into the formula $$NCR=Y/1-Y$$

Put another way, steps (b) and (c) may be combined into a single equation which may be solved directly for the NCR.

$$NCR = \frac{Y}{1-Y} = -\frac{(1000/W)\Delta + \frac{1}{M_2(x-1)}}{(1000/W)\Delta + \frac{1}{xM_1}}$$

The above procedure is relevant only to wash solution concentrations above the critical micelle concentration of the nonionic/cationic mixture. For concentrations which are as high as above five times the critical micelle concentration, $C_R$ is essentially independent of concentration. This means that for conventional laundry usage concentrations (e.g., 100 ppm to 10,000 ppm, and especially from about 250 ppm to about 3,000 ppm), the $C_R$ of most commercial cationic/nonionic surfactant mixtures (wherein the cationic component has CMC of less than about 100 ppm, measured at 105° F. water containing 7 grain/gallon of mixed calcium and magnesium hardness) will be independent of the actual usage concentration, so that using a concentration of about 1,000 ppm in the above calculation will be a satisfactory approximation for the entire range. As used herein, if a concentration range is not specified, the 1,000 ppm $C_R$ is meant.

By way of example, the optimum ratio for grease/oil removal for Composition a (palmitylalkyl trimethylammonium chloride+condensation product of $C_{12}$ alcohol with 5 moles of ethylene oxide) of Example I of concurrently filed U.S. Patent Application Ser. No. 919,181, Murphy, given $C_R$, is calculated below. For this system, the following values are either known or selected as indicated:

$W=1{,}000$ ppm (selected as representative of usage conditions)

$c_1^*=1.967\times10^{-5}$ ppm $c_2^*=2.1875\times10^{-5}$ ppm $\beta=-2.8$ $M_1=406.7$ $M_2=320$ $C_R=0.0073$ (selected for optimum greasy/oily soil removal performance, but could be any value between 0.002 and 0.2)

Substituting the values for $\beta$ and $C_R$ into equation (a):

$$(1-x)e^{-2.8x^2}=0.0073.$$

Solving iteratively for x, it is found that $x=0.922$. Using this value for x, it is found that $$f_1=0.983$$

$$f_2=0.0925$$

$$\Delta=(0.0925)(2.1875\times10^{-5})-(0.983)(1.967\times10^{-5})=-1.73\times10^{-5}$$

Substituting these values into equation (b), it is found that:

$$\frac{Y(1-0.922)}{406.7} - \frac{0.922(1-Y)}{320} =$$

-continued $$\frac{1000}{1000}(0.922)(0.922-1)(-1.73\times10^{-5})$$

$$Y=0.938$$

Substituting this value for Y into equation (c), the nonionic/cationic ratio is determined.

$$NCR=0.938/1-0.938=15.1$$

It will be noted that this ratio corresponds to the ratio actually found in Example I, Composition A.

In addition to these reduced cationic monomer criteria, the nonionic/cationic surfactant mixture may also satisfy the specific cloud point requirements, given below. In addition to outstanding particulate soil detergency, these preferred compositions will be optimized for the removal of greasy/oily soils. Thus, in preferred compositions, the cloud point of the nonionic/cationic mixture (and in preferred embodiments the nonionic/-cationic mixture plus any electrolytes present in the composition) falls between about 0° and about 95° C., preferably between about 10° and about 70° C., more preferably between about 20° and about 70° C., especially between about 30° and about 50° C. For cold water detergency, the surfactant mixture should have a cloud point between about 0° and about 25° C. The fact that a composition has a cloud point within these temperature ranges assures that the composition can be utilized under laundry temperature conditions to achieve outstanding removal of greasy/oily soils. If a composition does not have a cloud point within the temperature range specified, it will not yield outstanding greasy/oily soil cleaning within that temperature range. The compositions will exhibit their best grease/oil removal performance when the temperature of the wash solution in which they are used falls within about 20° C., preferably within about 15° C., and most preferably within about 10° C., of the cloud point of the nonionic/cationic surfactant mixture. Put another way, the laundry solution temperature range in which the preferred compositions deliver optimum grease/oil removal lies between the cloud point temperature of the system in the absence of the cationic component, and about 30° C., preferably about 25° C., most preferably about 20° C., above that cloud point temperature.

As used herein, the erm "cloud point" means the temperature at which a graph which plots the light scattering intensity of the composition versus wash solution temperature begins to sharply increase to its maximum value, under the following experimental conditions:

The light scattering intensity is measured using a Model VM-12397 Photogoniodiffusometer, manufactured by Societé Francaise d'instruments de controle et d'analyses, France (the instrument being hereinafter referred to as (SOFICA). The SOFICA sample cell and its lid are washed with hot acetone and allowed to dry. The surfactant mixture is made and put into solution with distilled water at a concentration of 1000 ppm. Approximately a 15 ml. sample of the solution is placed into the sample cell, using a syringe with a 0.2μ nucleopore filter. The syringe needle passes through the sample cell lid, so that the cell interior is not exposed to atomospheric dust. The sample is kept in a variable temperature bath, and both the bath and the sample are subject to constant stirring. The bath temperature is heated using the SOFICA's heater and cooled by the addition of ice (heating rate 1° C./minute); the temperature of the sample is determined by the temperature of the bath. The light scattering intensity of the sample is then determined at various temperatures, using a green filter and no polarizer in the SOFICA.

Fatty Amide Component

In particular preferred embodiments of the present invention the nonionic surfactant/cationic surfactant mixture additionally contains from about 2 to about 25%, preferably from about 2 to about 16%, and most preferably from about 3 to about 10%, of a fatty amide surfactant. Any nonionic surfactant conventionally used in detergent compositions may be used in these compositions; however, preferred compositions contain the nonionic surfactants defined above, in order to maximize the cleaning benefit obtained. These amide surfactants may be used in nonionic/cationic surfactant mixtures having nonionic:cationic ratios of from about 1:1 to about 100:1. When they are used in the compositions of the present invention, the mixtures have nonionic:cationic ratios of from 5:1 to about 1:1, preferably from 5:1 to about 5:3, more preferably about 10:3 to about 10:5, particularly about 10:4. In nonionic/cationic systems, the ratio of the total cationic and nonionic components to the amide component in the composition is in the range of from 5:1 to about 50:1, preferably from about 8:1 to 25:1. When these compositions are formulated in accordance with the ratio and the preferred reduced cationic monomer concentration limits given herein, they result in excellent particulate soil removal performance, as well as improved soil anti-redeposition characteristics, and the development is described in U.S. Patent Application Ser. No. 919,340, Cambre, filed of even date and incorporated hereby by reference, which is a continuation-in-part of U.S. Patent Application Ser. No. 811,419, filed June 29, 1977, now abandoned.

Amides useful in these preferred compositions include, but are not limited to, carboxylic acid amides, sulfonic acid amides, phosphonic acid amides, and boronic acid amides. Preferred amides include those having the formulae:

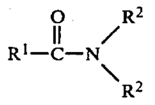 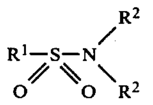

wherein $R^1$ is a $C_8$–$C_{20}$ alkyl, alkenyl, alkyl phenyl or alkyl benzyl group, preferably $C_{10}$–$C_{18}$ alkyl, and most preferably $C_{11}$ alkyl; and each $R^2$ is hydrogen, or $C_1$–$C_8$ alkyl or hydroxyalkyl, preferably hydrogen. Specific examples of these compositions include a mixture of stearoyl choline bromide (present in the washing solution at 120 parts per million), the condensation product of coconut alcohol with 5 moles of ethylene oxide (present in the wash solution at about 357 parts per million), and a mid-cut coconut alkyl ammonia amide ($R^1$=coconut alkyl and $R^2$ is hydrogen; present in the wash solution at about 50 parts per million); and a mixture of stearoyl choline bromide (100 ppm), the condensation product of coconut alcohol with 5 moles of ethylene oxide (357 ppm), and lauramide ($R^1$=$C_{11}$ and $R^2$ is hydrogen; at 45 ppm). These amides may also be used in the surfactant mixtures described in U.S. Patent Application Ser. No. 919,181, Murphy, filed of even date, and incorporated herein by reference, which have nonionic:cationic ratios of from 5.1:1 to about 100:1, preferably from 5.1:1 to about 50:1, particularly from about 6:1 to about 40:1, and most particularly from about 6:1 to about 20:1. In forming such compositions, which are optimized for the removal of greasy/oily soils, the nonionic/cationic surfactant mixture should have a cloud point of from about 0° to about 95° C., preferably from about 10° to about 70° C., especially from about 20° to about 70° C., and the surfactant mixture preferably has a ratio which corresponds to a reduced cationic monomer concentration of from about 0.002 to about 0.2, especially from about 0.002 to about 0.15, particularly from about 0.002 to about 0.08.

Additional Components

While the compositions of the present invention may contain additive materials conventionally used in detergent compositions, the amount of anion-producing materials, and hence anions, which will make the particular cationic surfactant used in the compositions non-water dispersible should be minimized. Whether a particular anion constitutes an "interfering anion" depends upon the physical and chemical properties (such as structure and dissociation constant) of the particular anions and cationic surfactants used in a given composition. It is preferred that anionic materials be contained in amounts sufficiently small such that not more than about 10 molar percent, preferably not more than about 5 molar percent, of the cationic surfactant contained in the laundry solution, is complexed by the anionic material. Such a complexing of the anionic material with the cationic surfactant decreases the overall cleaning and fabric conditioning performance of the composition.

Suitable anionic materials may be selected based on their strength of complexation with the cationic material included in the composition (as indicated by their dissociation constant). Thus, when an anionic material has a dissociation constant of at least about $1\times10^{-3}$ (such as sodium toluene sulfonate), it may be contained in an amount up to about 40%, by weight, of the cationic surfactant; where the anionic material has a dissociation constant of at least about $1\times10^{-5}$, but less than about $1\times10^{-3}$, it may be contained in an amount up to about 15%, by weight, of the cationic surfactant; and where the anionic material has a dissociation constant of less than about 1×10hu −5, (such as sodium $C_{11.8}$ linear alkylbenzene sulfonate), it should be contained only in amounts up to about 10%, by weight, of the cationic surfactant.

It is preferred, in order to minimize the effects of interfering anions, that the compositions of the present invention be substantially free of phosphate, polyphosphate, silicate, and polycarboxylate builder anionis, carboxymethyl cellulose, and anionic surfactants; particularly preferred are those which are substantially free of phosphate polyphosphate, and carboxymethyl cellulose materials. The compositions of the present invention contain from 0 to about 20% of phosphate materials; and, even though they contain no or low levels of phosphate materials, exhibit an outstanding level of particulate soil removal. It is preferred that the compositions be substantially free of phosphate materials both for performance and environmental reasons.

The compositions of the present invention may also contain additional ingredients generally found in laundry detergent compositions, consistent with the restrictions on interfering anions, stated above, at their conventional art-established levels. Very low levels (i.e., from about 1 to about 15%) of electrolytes, such as perborates, phosphates, polyphosphonates, carbonates or sulfates, may have a beneficial effect on cleaning performance.

The compositions of the present invention may contain up to about 15%, preferably up to about 5%, and most preferably from about 0.1 to 2%, of a suds suppressor component. Typical studs suppressors include long chain fatty acids, such as those described in U.S. Pat. No. 2,954,347, issued Sept. 27, 1960, St. John, and combinations of certain nonionics therewith, as disclosed in U.S. Pat. No. 2,954,348, issued Sept. 27, 1960, Schwoeppe, both disclosures being incorporated herein by reference. Other suds suppressor components useful in the compositions of the present invention include, but are not limited to, those described below.

Preferred suds suppressing additives are described in U.S. Pat. No. 3,933,672, issued Jan. 20, 1976, Bartolotta et al., incorporated herein by reference, relative to a silicone suds controlling agent. The silicone material can be represented by alkylated polysiloxane materials such as silica aerogels and xerogels and hydrophobic silicas of various types. The silicone material can be described as a siloxane having the formula:

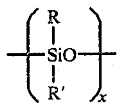

wherein x is from about 20 to about 2,000, and R and R' are each alkyl or aryl groups, especially methyl, ethyl, propyl, butyl and phenyl. The polydimethylsiloxanes (R and R' are methyl) having a molecular weight within the range of from about 200 to about 200,000, and higher, are all useful as suds controlling agents. Additional suitable silicone materials wherein the side chain groups R and R' are alkyl, aryl, or mixed alkyl and aryl hydrocarbyl groups exhibit useful suds controlling properties. Examples of the like ingredients include diethyl-, dipropyl-, dibutyl-, methyl-ethyl-, phenylmethyl-polysiloxanes and the like. Additional useful silicone suds controlling agents can be represented by a mixture of an alkylated siloxane, as referred to hereinbefore, and solid silica. Such mixtures are prepared by affixing the silicone to the surface of the solid silica. A preferred silicone suds controlling agent is represented by a hydrophobic silanated (most preferably trimethylsilanted) silica having a particle size in the range from about 10 millimicrons to 20 millimicrons and a specific surface are above about 50 $m^2$/gm. intimately admixed with dimethyl silicone fluid having a molecular weight in the range from about 500 to about 200,000 at a weight ratio of silicone to silanated silica of from about 19:1 to about 1:2. The silicone suds suppressing agent is advantageously releasably incorporated in a water-soluble or water-dispersible, substantially non-surface-active detergent-impermeable carrier.

Particularly useful suds suppressors are the self-emulsifying silicone suds suppresors, described in U.S. Patent Application Ser. No. 841,078, Gault et al, filed Oct. 11, 1977, now U.S. Pat. No. 4,136,045, issued Jan. 23, 1979 which is a continuation-in-part of U.S. Patent Application Ser. No. 622,303, filed Oct. 14, 1975, now abandoned both of which are incorporated herein by reference. An example of such a compound is DB-544, commercially available from Dow Corning, which contains a siloxane/glycol copolymer together with solid silica and a siloxane resin.

Microcrystalline waxes having a melting point in the range from 35° C.-115° C. and a saponification value of less than 100 represent additional examples of a preferred suds regulating component for use in the subject compositions, such waxes are described in U.S. Pat. No. 4,056,481, Tate, issued Nov. 1, 1977, incorporated herein by reference. The microcrystalline waxe are substantially water-insoluble, but are water-dispersible in the presence of organic surfactants. Preferred microcrystalline waxes have a melting point from about 65° C. to 100° C., a molecular weight in the range from 400-1,000; and a penetration value of at least 6, measured at 77° F. by ASTM-D1321. Suitable examples of the above waxes include: microcrystalline and oxidized microcrystalline petrolatum waxes; Fischer-Tropsch an oxidized Fisher-Tropsch waxes; ozokerite; ceresin; montan wax; beeswax; candelilla; and carnauba wax.

Alkyl phosphate errors represent an additional preferred suds suppressant for use herein. These preferred phosphate esters are predominantly monostearyl phosphate which, in addition thereto, can contain di- and tristearyl phosphates and monooleyl phosphates, which can contain di- and trioleyl phosphates.

The alkyl phosphate esters frequently contain some trialkyl phosphate. Accordingly, a preferred phosphate ester can contain, in addition to the monoalkyl ester, e.g., monostearyl phosphate, up to about 50 mole percent of dialkyl phosphate and up to about 5 mole percent of trialkyl phosphate Other compatible adjunct components which may be included in the compositions of the present invention, in their conventional art-established levels of use, include bleaching agents, bleach activators, soil suspending agents, corrosion inhibitors, dyes, fillers, optical brighteners, germicides, pH adjusting agents, enzymes, enzyme stabilizing agents, perfumes, fabric softening components, static control agents, and the like. However, because of the numerous and diverse performance advantages of the compositions of the present invention, many components, such as static control agents, fabric softening agents and germicides, will not usually be necessary.

The compositions of the present invention may be manufactured and used in a variety of physical forms, such as solid, powder, granular, paste, or liquid. The compositions are particularly well-suited for incorporation into substrate articles for use in the home laundering process. Examples of such articles are described in U.S. Pat. Application Ser. No. 781,378, Flesher et al, filed Mar. 25, 1977; U.S. Pat. Application Ser. No. 781,400, Jones et al, filed Mar. 25, 1977, now U.S. Pat. No. 4,095,946, issued June 20, 1978; U.S. Pat. Application Ser. No. 781,399, Jones, filed Mar. 25, 1977, now U.S. Pat. No. 4,118,525, issued Oct. 3, 1978; and U.S. Pat. Application Ser. No. 781,385, Hagner et al, filed Mar. 25, 1977, now US. Pat. No. 4,113,630, issued Sept. 12, 1978all of the disclosures of which are incorporated herein by reference. These articles consist of a water-insoluble substrate which releasably incorporates an effective amount, preferably from about 3 to 120 grams, particularly from about 20 to 80 grams, of the detergent compositions of the present invention. A particularly preferred substrate article incorporates a bleaching component and a bleach activator on the substrate, together with the nonionic/cationic surfactant mixture.

In a particularly preferred method of making the detergent compositions of the present invention, the specifically defined nonionic and cationic surfactants, present in ratios from about 1:1 to about 100:1, are intimately and completely mixed at a temperature of from about 25° C. to about 95° C., preferably from about 40° C. to about 90° C., prior to the addition of any additional components. By using this process, the components are taken from their original liquid or powder form and are made into a thick paste, which is ideally suited for use in the substrate articles, described above. This process is described and claimed in concurrently filed U.S. Patent Application Ser. No. 919,339, Cockrell and Cambre, incorporated herein by reference, which is a continuation-in-part of U.S. Pat. Application Ser. No. 811,418, filed June 29, 1977, now abandoned.

When this process is used to make the compositions of the present invention, the components are present in nonionic:cationic ratios of from 5:1 to about 1:1, preferably from 5:1 to about 5:3, and more preferably from about 10:3 to about 10:5, and are formed into mixtures which satisfy the reduced cationic monomer concentration requirements, herein. In one particularly preferred embodiment of this process, the components are intimately mixed together at a temperature of about 25° C. In this embodiment, it is preferred that the anion contained in the cationic surfactant be bromide. Thus, when stearoyl choline bromide, a powder having the following formula,

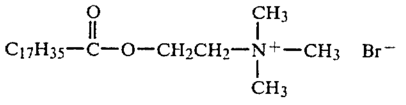

is intimately mixed at a temperature of about 25° C. with the condensation product of $C_{12}$ alcohol with 5 moles of ethylene oxide, a liquid, at a nonionic: cationic ratio of about 10:4, a thick paste product is formed. Substantially similar results are obtained when the nonionic surfactant is the condensation product of coconut alcohol with 5 moles of ethylene oxide.

In another particularly preferred embodiment of this process, the components are intimately mixed together at a temperature of at least about 65° C. In this embodiment, it is preferred that the anion contained in the cationic surfactant be chloride. Thus, when stearoyl choline chloride, a powder, is intimately mixed at a temperature of about 80° C. with the condensation product of $C_{12}$ alcohol with 5 moles of ethylene oxide, a liquid, at a nonionic:cationic ratio of about 10:4, a thick paste product is formed. If the same components are mixed together at about 25° C., the mixture remains a liquid, which is much less desirable for use in making substrate articles. Substantially similar results are obtained when the nonionic surfactant is the condensation product of coconut alcohol with 5 moles of ethylene oxide. Where this process is used in making the compositions described in concurrently filed U.S. Patent Application Ser. No. 919,181, Murphy, incorporated herein by reference, nonionic:cationic ratios of from 5.1:1 to about 100:1, preferably from 5.1:1 to about 50:1, more preferably from about 6:1 to about 40:1, and most preferably from about 6:1 to about 20:1, are used, in accordance with the cloud point and the preferred reduced cationic monomer concentration definitions, state therein.

The compositions of the present invention are used in the laundering process by forming an aqueous solution (preferably one having a temperature of from about 10° to about 50° C.) containing from about 0.01 (100 parts per million) to 0.3% (3,000 ppm), preferably from about 0.02 to 0.2%, and most preferably from about 0.03 to about 0.15%, of the nonionic/cationic detergent mixture, and agitating the soiled fabrics in that solution. The fabrics are then rinsed and dried. When used in this manner, the compositions of the present invention yield exceptionally good particulate soil removal performance. Further, the compositions also provide fabric softening, static control, and dye transfer inhibition benefits to the fabrics laundered therewith.

Although not intending to be bound by theory, it is believed that the clay removal mechanism is as follows. At the optimum nonionic:cationic ratio, as defined by the reduced cationic monomer concentration, the cationic surfactant adsorbs onto the clay soil (negatively-charged) in a mono-layer, neutralizing the charge. This neutralized charge results in a hydrophobic surface which increases the adsorption of the nonionic surfactant onto the clay surface. The clay soil is then easily removed by the agitation.

It has been found that when the nonionic/cationic compositions of the present invention are used in a laundry solution, a threshold concentration of at least about 50, preferably about 100, most preferably about 150, parts per million on the cationic component must be present in the laundry solution in order to give the particulate soil removal benefit. Under conventional United States laundry conditions, which generally utlize from about 150 to 1500 parts per million of a detergent composition in the laundry solution, nonionic surfactant to cationic surfactant ratios of from 5:1 to about 1:1 are necessary in order to provide this threshold concentration in the laundry solution. In washing processes which utilize higher concentrations of detergent composition, such as European washing processes, it is possible to use higher nonionic surfactant to cationic surfactant ratios, while still attaining the necessary cationic threshold concentration. Under these European washing conditions it is possible to obtain excellent particulate soil removal, in addition to outstanding greasy and oily soil and body soil removal, using the nonionic surfactant to cationic surfactant ratios of from 5.1:1 to about 100:1 defined in concurrently filed U.S. Patent Application Ser. No. 919,181 Murphy, incorporated herein by reference.

All percentages, parts, and ratios used herein are by weight unless otherwise specified.

The following nonlimiting examples illustrate the compositions and the method of the present invention.

EXAMPLE I

Identical cotton, polyester/cotton, and polyester swatches were stained with a clay-in-water suspension and three stained swatches of each fabric type were washed in a one gallon washing machine, which simulates the action of a commercial washing machine, using two different detergent compositions. One set of swatches was laundered using the commercially available built, brightener-containing laundry detergent Tide, marketed by The Procter & Gamble Company, at the equivalent of its recommended 1¼ cup usage level. The second set of swatches was laundered in a detergent composition of the present invention, having the following formulation:

| Component | % by Weight |
|---|---|
| Dicoconutalkyl dimethyl-ammonium bromide | 19 |
| Condensation product of $C_{14-15}$ alcohol with 7 moles of ethylene oxide (Neodol 45-7) HLB = 11.5 | 48 |
| Sodium chloride | 33 |

$C_R = 0.0815$

This detergent composition, having a nonionic: cationic ratio of about 10:4, was used in the aqueous laundering solution at a concentration of about 500 ppm, and had a pH in the laundry solution of about 6.5. The wash water contained 7 grains per gallon of mixed calcium and magnesium hardness, and the laundering operation lasted for 10 minutes at 100° F. (38° C.). A Hunter Reflectometer was then used to obtain a reflectance reading for each of the laundered swatches. The cleaning effectiveness of the particular treatment was determined by averaging the reflectance readings of the individual swatches. A higher reflectance reading indicates greater cleaning effectiveness.

This procedure was repeated twice for each of the two detergent compositions and the reflectance readings were averaged for the two runs. The conventional built phosphate granular detergent yielded fabrics having an average of 63.1 Hunter Whiteness Units, while the detergent composition of the present invention yielded fabrics having a value of 62.0 Hunter Whiteness Units. These data demonstrate the outstanding clay soil removal performance of the unbuilt compositions of the present invention, which equaled the performance provided by the conventional built, brightener-containing detergent composition.

Substantially similar cleaning results are obtained where the detergent composition of the present invention does not contain the sodium chloride component, indicating that for the particular detergent composition defined above, sodium chloride does not contribute ∓interfering anions" to the laundry solution of the disclosed detergent compositions.

Substantially similar results are also obtained where the cationic surfactant used in the above composition is replaced by $C_{12}$ alkyl trimethylammonium chloride, $C_{14}$ alkyl trimethylammonium bromide, di-$C_{10}$ alkyl dimethylammonium chloride, di-$C_{12}$ alkyl dimethylammonium chloride, tri-$C_8$ alkyl methylammonium bromide, tri-$C_{10}$ alkyl methylammonium chloride, or the cationic surfactants listed below:

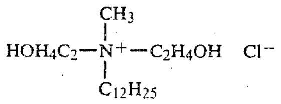

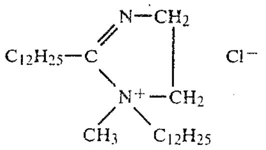

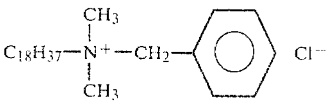

-continued

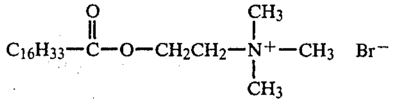

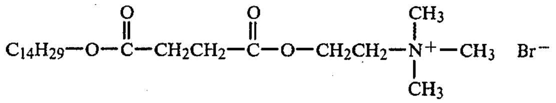

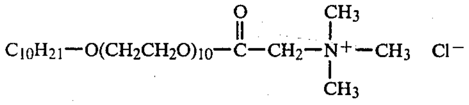

Substantially similar cleaning results are also obtained where the cationic surfactant used above is replaced by a mixture of dicoconutalkyl dimethylammonium bromide (A) together with $C_{12}$ alkyl trimethylammonium chloride (B) in a ratio of A:B of about 4:1, 3:1, 2:1, 1:1, 1:2, or 1:4; a mixture of

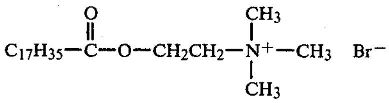 (C)

together with di-$C_{10}$ alkyl dimethylammonium chloride (D) in a ratio of C:D of about 5:1, 3:1, 1:1, 1:3 or 1:5; or a mixture of C, above, together with

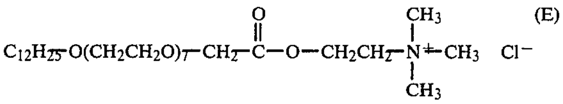 (E)

in a ratio of C:E of about 7:1, 3:1, 2:1, 1:1, 1:2, 1:3, 1:4, or 1:7.

Essentially similar results are also obtained where the nonionic component of the above composition is replaced with the condensation product of $C_{10}$ alcohol with 3 moles of ethylene oxide (HLB=9), the condensation product of coconut alcohol with 5 moles of ethylene oxide, the condensation product of coconut alcohol with 7 moles of ethylene oxide (HLB=12.8), the condensation product of ($C_{12-13}$ alcohol with 6.5 moles of ethylene oxide (HLB=12), the condensation product of $C_{12-13}$ alcohol with 3 moles of ethylene oxide (HLB=7.9), and the same product which is stripped so as to remove unethoxylated and lower ethoxylate fractions, the condensation product of $C_{12}$ alcohol with 5 moles of ethylene oxide, the condensation product of $C_{12-13}$ alcohol with 9 moles of ethylene oxide, and the condensation product of $C_{14-15}$ alcohol with 3, 4 or 9 moles of ethylene oxide. A mixture of the condensation product of $C_{14-15}$ alcohol with 3 moles of ethylene oxide together with the condensation product of $C_{14-15}$ alcohol with 7 moles of ethylene oxide in a ratio of lower ethoxylate nonionic to higher ethoxylate nonionic of about 2:1, or the mixture of the condensation product of coconut alcohol with 5 moles of ethylene oxide together with an alkyl glyceryl ether having the structural formula:

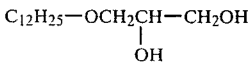

in a ratio of alcohol ethoxylate to glyceryl ether of about 7:3.

Results substantially equivalent to those obtained above are also obtained where the detergent composition has a ratio of nonionic surfactant to cationic surfactant of 1:1, 10:3, 5:3, 10:5, or 5:1.

Substantially similar results are also obtained where the detergent composition is formulated, such as by the addition of monoethanolamine, to have a pH in the laundry solution of about 7, 8, 8.5, 9 or 10.

EXAMPLE II

Identical cotton, polyester/cotton, and polyester swatches were stained with bacon grease and dirty motor oil and were aged for about 24 hours. The swatches were then washed in a one gallon washing machine, which simulates the action of a commercial washing machine, using two different detergent compositions. The first group of swatches was washed using a heavy-duty liquid laundry detergent composition, optimized for grease and oil removal, having the formulation given below, at its recommended usage level.

| Component | % by Weight |
|---|---|
| Neodol 45-7 | 15.0 |
| Mg Linear alkyl benzene sulfonate | 31.3 |
| Triethanolamine | 3.5 |
| Ethanol | 6.5 |
| Coconut alkyl fatty acid | 1.0 |
| Water | 41.8 |
| Brightener and minors (brighteners, perfume, etc.) | Balance to 100 |

The second group of swatches was washed in a laundry detergent composition of the present invention having the following formulation:

| Component | % by Weight |
|---|---|
| 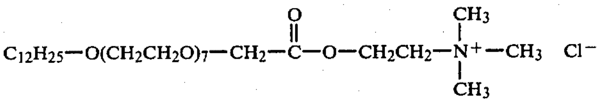 | 28.6 |
| Condensation product of $C_{12-13}$ alcohol with 3 moles of ethylene oxide, stripped to remove lower ethoxylate and unethoxylated fractions (Neodol 23-3T) | 71.4 |

The detergent composition of the present invention had a ratio of nonionic surfactant to cationic surfactant of about 10:4 and was used in the aqueous laundering solution at a concentration of about 500 ppm, having a pH in the laundry solution of about 6.5. The fabrics were washed for about 10 minutes in water having a temperature of about 100° F. (38° C.), containing 7 grains per gallon of mixed calcium and magnesium hardness. The percentage stain removal for each swatch was calculated using light reflectance readings, obtained on a Gardner color measurement device, taken before and after the washing process. The average percent stain removal for each of the detergent compositions tested is summarized in the table below:

| | Average % Stain Removal (across 3 fabric types) | |
|---|---|---|
| | Bacon Grease | Dirty Motor Oil |
| Liquid laundry composition | 58.2 | 45.5 |
| Nonionic/cationic mixture | 58.8 | 57.5 |

These data demonstrate the effective grease and oil removal obtained using the preferred cationic components in the detergent compositions of the present invention. The detergent composition of the present invention, as formulated above, also yields excellent particulate soil removal performance, and gives fabric softening, static control and dye transfer inhibition benefits to fabrics laundered therewith.

Substantially similar results are obtained where the nonionic component of the above composition is replaced by the condensation product of $C_{10}$ alcohol with 3 moles of ethylene oxide, the condensation product of $C_{12}$ alcohol with 5 moles of ethylene oxide (HLB=11), the condensation product of coconut alcohol with 5 moles of ethylene oxide, the condensation product of coconut alcohol with 7 moles of ethylene oxide, the condensation product of $C_{12-13}$ alcohol with 6.5 moles of ethylene oxide, or the condensation product of $C_{14-15}$ alcohol with 7 moles of ethylene oxide.

Substantially similar results are also obtained when the ratio of nonionic surfactant to cationic surfactant used in the above composition is 10:3, 20:7, 10:5, 20:11, 5:3, 5:4, or 1:1.

Similar results are also obtained where the cationic surfactant, used above, is replaced by one of the following surfactants:

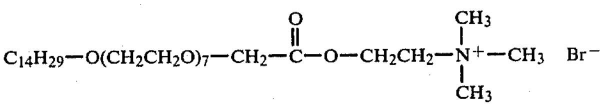

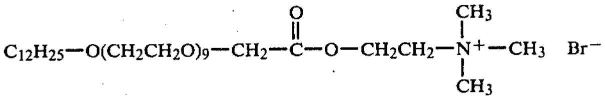

-continued

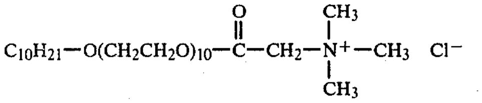

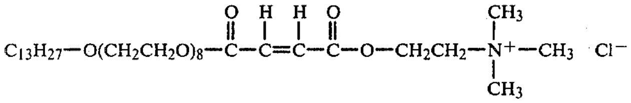

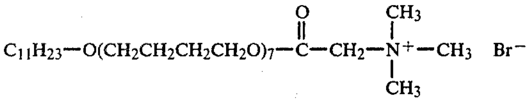

EXAMPLE III

A detergent composition of the present invention was formulated by combining the condensation product of coconut alcohol with 5 moles of ethylene oxide (HLB=10.5) together with one of the preferred cationic surfactants of the present invention having the formula:

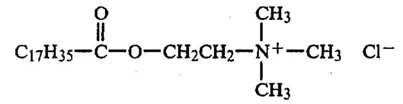

in a ratio of nonionic surfactant to cationic surfactant of about 10:4 ($C_R \approx 0.071$). This detergent composition had a pH in the wash solution of about 8.5, and was used in the washing solution at a concentration of about 500 ppm. A second detergent composition of the present invention was formulated by combining the same nonionic and cationic surfactants in the same ratio as above. The composition also contained monoethanolamine as an alkalinity source, in an amount such that the monoethanolamine was present at about 30 ppm in the washing solution when the entire composition was used at a concentration of about 530 ppm. The pH of the second detergent composition in the laundry solution was about 9.3.

Identical polyester/cotton blend swatches were stained with a mixture of soil collected from air conditioning filters and a mineral oil/olive oil/oleic acid blend. The stained swatches were then washed using each of the above two detergent compositions in a one gallon washing machine which simulates the action of a commercial washing machine. The washing operation was carried out for 10 minutes using water having a temperature of about 100° F. (38° C.) and containing 7 grains per gallon of mixed calcium and magnesium hardness.

The soil removal performance was calculated by using the weight removal percentage, averaged across the three stained swatches washed in each composition. Both compositions gave excellent soil removal performance. However, the cationic/nonionic mixture containing monoethanolamine and having the higher alkalinity had a soil removal of about 73%, while the lower pH cationic/nonionic mixture had a soil removal of about 50%. These data demonstrate that improved soil removal performance is otained by the use of cationic/nonionic detergent compositions having a higher alkalinity such as that obtained by the inclusion of monoethanolamine.

Substantially similar results are obtained when other sources of alkalinity, such as sodium hydroxide, sodium carbonate, triethanolamine, and sodium silicate, are used, in comparable amounts, in place of or in combination with the monoethanolamine.

Similar results are also obtained where the nonionic component used above is replaced by the condensation product of $C_{10}$ alcohol with 3 moles of ethylene oxide, the condensation product of coconut alcohol with 6 moles of ethylene oxide, the condensation product of coconut alcohol with 7 moles of ethylene oxide, the condensation product of $C_{12-13}$ alcohol with 6.5 moles of ethylene oxide, the condensation product of $C_{14-15}$ alcohol with 7 moles of ethylene oxide, or the condensation product of $C_{12-13}$ alcohol with 3 moles of ethylene oxide stripped so as to remove the lower ethoxylate and unethoxylated fractions.

Excellent cleaning results are also obtained where the detergent compositions used contain nonionic to cationic surfactant ratios of about 5:1, 4:1, 10:3, 20:7, 20:9, 2:1, 5:3, or 1:1.

Excellent cleaning results are also obtained where the nonionic component is replaced by a mixture of the condensation product of $C_{14-15}$ alcohol with 3 moles of ethylene oxide together with the condensation product of $C_{14-15}$ alcohol with 7 moles of ethylene oxide, in a ratio of lower ethoxylate nonionic to higher ethoxylate nonionic of about 2:1; or a mixture of the condensation product of coconut alcohol with 5 moles of ethylene oxide together with an alkylglyceryl ether having the formula:

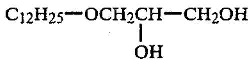

in a ratio of alcohol ethoxylate to glyceryl ether of about 7:3.

Substantially similar cleaning results are also obtained where the cationic component is replaced by $C_{12}$ alkyl trimethylammonium chloride, $C_{14}$ alkyl trimethylammonium bromide, di-$C_{10}$ alkyl dimethylammonium bromide, di-$C_{12}$ alkyl dimethylammonium chloride, tri-$C_8$ alkyl methylammonium bromide, tri-$C_{10}$ alkyl methylammonium chloride, or cationic components having the formulae given below:

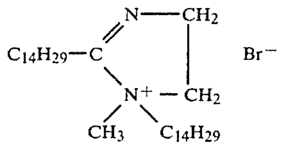

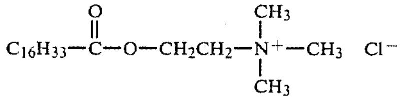

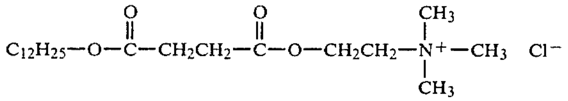

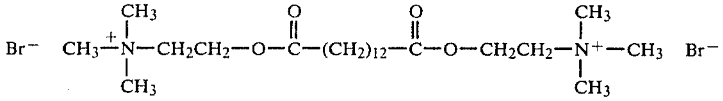

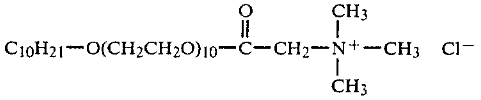

EXAMPLE IV

A detergent composition of the present invention was formulated by combining the condensation product of coconut alcohol with 5 moles of ethylene oxide together with the cationic surfactant having the formula:

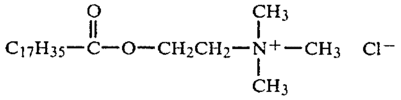

such that the ratio of nonionic surfactant to cationic surfactant was about 10:4. The detergent composition was used in the laundry solution at a concentration of about 500 ppm. A second detergent composition of the present invention was formulated so as to contain the same nonionic and cationic components in the same ratio, but which additionally contained a $C_{12-16}$ alkyl fatty acid ammonia amide, present in an amount such that the amide component would be present in the washing solution at a concentration of 50 ppm when the composition was used at a concentration of 500 ppm. This composition had a pH in the laundry solution of about 8.4. Nine swatches (3 cotton, 3 polyester, and 3 polyester/cotton blend), were stained with a clay-in-water suspension and were washed in a one gallon washing machine which simulates the action of a commercial washing machine, using each of the above two detergent compositions. Two 11"×11"100% cotton terry cloths, with loop construction, were added to each washing machine as redeposition sites for the soil removed from the stained swatches. The washing process was carried out for 10 minutes in water of about 100° F. (38° C.), containing 6.5 grains per gallon of mixed calcium and magnesium hardness. After washing the cloths in the respective test treatments and subsequently drying them, the reflectance of the terry cloths were read using a Hunter Reflectometer. The cleaning performance of both detergent compositions on the stained swatches was excellent. In addition, the first composition, containing only the nonionic and cationic components, yielded terry cloths having a reflectance of 53 Hunter Whiteness Units, while the second composition, which additionally contained the amide component, yielded terry cloths having a reflectance of 71 Hunter Whitness Units. These data demonstrate the improved soil antiredeposition properties which are obtained by the inclusion of an amide component in the cationic/nonionic detergent compositions of the present invention.

Substantially similar results are obtained where the amide component is present in such an amount such that the concentration of amide in the washing solution is about 80 ppm, 75 ppm, 65 ppm, 55 ppm, 40 ppm, or 30 ppm. Similar results are also obtained where the amide component used above is replaced by amides having the formula:

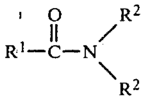 or 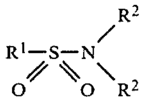

wherein $R^1$ is $C_8$ alkyl, $C_{10}$ alkyl, $C_{12}$ alkyl, $C_{13}$ alkyl, $C_{15}$ alkyl or $C_{17}$ alkyl, and $R^2$ is hydrogen, methyl, ethyl, propyl, or hydroxymethyl.

Excellent results are also obtained where the nonionic surfactant used above is replaced by the condensation product of $C_{10}$ alcohol with 3 moles of ethylene oxide, the condensation product of coconut alcohol with 6 moles of ethylene oxide, the condensation product of coconut alcohol with 7 moles of ethylene oxide, the condensation product of $C_{12-13}$ alcohol with 6.5 moles of ethylene oxide, the condensation product of $C_{14-15}$ alcohol with 7 moles of ethylene oxide, or the condensation product of $C_{12-13}$ alcohol with 3 moles of ethylene oxide stripped so as to remove nonethoxylated and lower ethoxylate fractions. Excellent results are also obtained wherein the nonionic component is replaced by a mixture of the condensation product of $C_{10}$ alcohol with 3 moles of ethylene oxide together with the condensation product of a secondary $C_{15}$ alcohol with 9 moles of ethylene oxide, in a ratio of lower ehoxylate nonionic to higher ethoxylate nonionic of about 3:1; or the mixture of the condensation product of coconut alcohol with 5 moles of ethylene oxide together with an alkyl glyceryl ether having the formula:

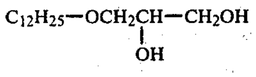

wherein the ratio of nonionic surfactant to glyceryl ether is about 3:1.

Substantially similar results are also obtained wherein the ratio of nonionic surfactant to cationic surfactant in the above compositions is 5:1, 10:3, 20:7, 20:9, 2:1, 5:3, or 1:1.

Excellent results are also obtained where the cationic component of the above compositions is replaced by $C_{12}$ alkyl trimethylammonium chloride, $C_{14}$ alkyl trimethylammonium chloride, di-$C_{10}$ alkyl dimethylammonium bromide, di-$C_{12}$ alkyl dimethylammonium bromide, tri-$C_8$ alkyl methylammonium chloride, or tri-$C_{10}$ alkyl methylammonium bromide.

EXAMPLE V

A substrate article, for use in the automatic laundering operation, is made by coating one side of an 8"×11" sheet of a Scott 8050 Industrial Towel, having an air permeability of about 130 cu. ft./min./sq. ft., a basis weight of about 77.5 grams per sq. yd., and a thickness of 44 mils, with about 50 grams of a composition having the formulation given below. The composition is made by intimately mixing the nonionic and cationic surfactants together, at a temperature of about 80° C., to form a thick paste, and then adding the remaining components.

| Component | Weight % |
|---|---|
| 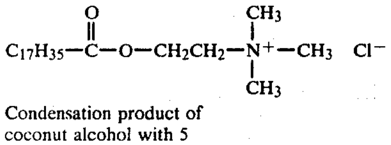 | 24.6 |
| Condensation product of coconut alcohol with 5 moles of ethylene oxide | 61.6 |
| $C_{12-16}$ alkyl fatty acid ammonia amide | 8.6 |
| Monoethanolamine | 5.2 |
| $C_R$ = 0.057 | |

An identical sheet of the paper towel is placed on top of the coated original sheet, and the edges are sewn together so as to enclose the composition. This article has a pH in the laundry solution of about 9.5, and provides a convenient method for introducing the compositions of the present invention into the laundering solution, as well as providing excellent cleaning performance.

A substrate article may also be made by coating one side of an 11"×11" sheet of melt-blown polypropylene, having a thickness of about 29 mils, a basis weight of about 58.5 grams per sq. yd., and an air permeability of about 66 cu.ft./min./sq. ft., with about 60 grams of the detergent composition described above, placing an identical substrate sheet over the coated sheet, and heat-sealing together the edges of the two substrates, enclosing the detergent composition within the article.

Similar articles may be manufactured wherein the cationic surfactant is stearoyl chloine bromide. In this case, the cationic and nonionic surfactants are intimately mixed at a temperature of about 25° C., to form a thick paste, and the remaining components are added.

EXAMPLE VI

A heavy-duty liquid laundry detergent composition, having the formula given below, is formulated by mixing together the following components in the stated proportions.

| Component | Weight % |
|---|---|
| 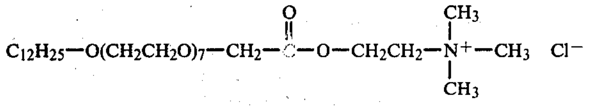 | 14.3 |
| Condensation product of coconut alcohol with 5 moles of ethylene oxide | 35.7 |
| Monoethanolamine | 45.0 |
| Lauramide | 4.0 |
| Minors (suds suppressor, perfume brightener, etc.) | 1.0 |
| $C_R$ = 0.026 | |

This product, when used in an automatic laundering operation at a concentration of about 0.05%, has a pH of about 9.5 and provides excellent removal of both particulate and greasy/oily soils, as well as exhibiting good antiredeposition properties.

EXAMPLE VII

A solid particulate detergent composition of the present invention, having the formulation given below, is made by mixing together the following components.

| Component | Weight % |
|---|---|
| Dicoconut alkyl dimethylamonium bromide | 14.3 |
| Condensation product of coconut alcohol with 5 moles of ethylene oxide | 35.7 |
| Sodium bicarbonate | 45.0 |
| $C_{12-16}$ alkyl fatty acid ammonia amide | 4.0 |
| Minors (suds suppressor, perfume, (etc.) | 1.0 |

$C_R$ = 0.0466

This product, when used in an automatic laundering operation, at conventional usage concentrations, has a pH of about 10, and provides excellent particulate soil removal. It is to be noted that as to the detergent composition, defined above, bicarbonate anions do not constitute "interfering anions" (i.e., excellent performance is obtained even when such anions are present in the laundry solution).

EXAMPLE VIII

A cationic surfactant having the formula given below is prepared as follows.

$$C_{12}H_{25}-O(CH_2CH_2O)_7-CH_2-\overset{\overset{O}{\|}}{C}-O-CH_2CH_2-\overset{\overset{CH_3}{|}}{\underset{\underset{CH_3}{|}}{N^+}}-CH_3 \quad Cl^-$$

44 Grams of an anhydrous sodium alkyl ethoxy acetate, having the formula given below and prepared by the azeotropic removal of water from Sandopan DTC Gel (Sandoz Chemical), were dissolved in 100 ml. of methylene chloride at room temperature.

$$C_{12}H_{25}-O(CH_2CH_2O)_7CH_2-\overset{\overset{O}{\|}}{C}-O^- \quad Na^+$$

18.8 Grams of oxalyl chloride were added rapidly to the solution and the reaction mixture was left standing overnight. The solvent and the excess oxalyl chloride were then removed from the mixture by vacuum distillation, yielding the acid chloride corresponding to the sodium alkyl ethoxy acetate shown above.

40 Grams of the acid chloride product were then dissolved in 100 ml. of methylene chloride, in a two neck reaction vessel, equipped with a reflux condenser and dropping funnel. 12.2 Grams of N,N-dimethylaminoethanol were then added dropwise from the dropping funnel into the reaction mixture, at a rate such that the reaction heated to a boil. The reaction was stirred at reflux during the addition step, and was allowed to stir overnight at ambient temperature. The methyl chloride solution was then washed with an aqueous base solution, following by two water washes. The separated organic layer was dried over sodium sulfate, and then stripped under vacuum to yield about 39 grams of amine ester corresponding to the sodium alkyl ethoxy acetate compound described above.

37 Grams of this amine ester compound were then placed in a round bottom flask, equipped with a reflux condenser and a dropping funnel. An excess of iodomethane was added rapidly to the amine ester, causing the reaction mixture to boil during the addition. After the reaction subsided, the mixture was left standing overnight and was then stripped under vacuum, yielding 43 grams of the desired choline ester cationic surfactant having the formula given above.

This cationic surfactant, when used in the detergent compositions described herein, yields outstanding particulate soil removal, as well as excellent greasy and oily soil and body soil removal, in addition to providing static control, fabric softening, and dye transfer inhibition benefits to fabrics laundered with the compositions.

EXAMPLE IX

A stearic acid choline ester cationic surfactant, having the formula given below, was prepared in the following manner.

$$C_{17}H_{35}-\overset{\overset{O}{\|}}{C}-O-CH_2CH_2-\overset{\overset{CH_3}{|}}{\underset{\underset{CH_3}{|}}{N^+}}-CH_3 \quad Cl^-$$

200 Grams of stearic acid, 138 grams of N,N-dimethylaminoethanol, 6 grams of concentrated sulfuric acid and 2000 ml. of benzene were combined in a flask equipped with a Dean-Stark water trap and a reflux condenser. The mixture was stirred at reflux, through the water trap, for four days, during which time the theoretical amount of water had collected. The reaction mixture was cooled to room temperature and then washed with a dilute calcium hydroxide solution, following by three water washes. The solution was then dried over sodium sulfate and stripped under vacuum, yielding an amine ester.

The reaction product formed above was dissolved in 1000 ml. of 80/20 acetone/methylene chloride solvent. Methyl chloride was bubbled into the solution, which thickened as the quaternary ammonium ester began to precipitate out of solution. The reaction mixture was saturated with methylene chloride and then allowed to stand overnight. The white, crystalline solid product was isolated by vacuum filtration, washed with acetone, and then dried in a vacuum oven, yielding 185 grams of the desired stearoyl choline ester cationic surfactant.

This biodegradable cationic surfactant, when used in the detergent compositions defined herein, yields excellent particulate soil removal performance, as well as fabric softening, static control and dye transfer inhibition benefits to fabrics laundered with those compositions.

What is claimed is:

1. A compound having the formula $$R^3-O[(\overset{\overset{R^2}{|}}{C}H)_nO]_y-(Z^1)_a-(R^4)_t-Z^2-(CH_2)_m-\overset{\overset{R^1}{|}}{\underset{\underset{R^1}{|}}{N^+}}-R^1 \quad X^-$$

wherein each $R^1$ is $C_1$ to $C_4$ alkyl or hydroxyalkyl; each $R^2$ is either hydrogen or $C_1$ to $C_3$ alkyl; $R^3$ is $C_4$ to $C_{30}$ straight or branched chain alkyl or alkenyl; $R^4$ is $C_1$ to $C_{10}$ alkylene or alkenylene; n is from 2 to 4; y is from 1 to 20; a is 0 or 1, and t is 0 to 1, but t must be 1 when a is 1; m is from 1 to 5; $Z^2$ is selected from the group consisting of $$-O-\overset{\overset{O}{\|}}{C}-,\ -\overset{\overset{O}{\|}}{C}-O-,\ -\overset{\overset{O}{\|}}{C}-,\ -O-,$$
$$-O-\overset{\overset{O}{\|}}{C}-O-,\ -\overset{\overset{O}{\|}}{C}-\overset{\overset{H}{|}}{N}-,\ -\overset{\overset{H}{|}}{N}-\overset{\overset{O}{\|}}{C}-,$$
$$-O-\overset{\overset{O}{\|}}{C}-\overset{\overset{H}{|}}{N}-, \text{ and } -\overset{\overset{H}{|}}{N}-\overset{\overset{O}{\|}}{C}-O-$$

$Z^1$ is selected from the group consisting of $$-\overset{\overset{O}{\|}}{C}- \text{ and } -\overset{\overset{O}{\|}}{C}-\overset{\overset{H}{\|}}{N}-;$$

said selections being made so that $$R^3-O[(\overset{\overset{R^2}{|}}{C}H)_nO]_y-(Z^1)_a-(R^4)_t-Z^2-(CH_2)_m-$$

is an alkyl or alkenyl group which can be interrupted by only structures selected from the group consisting of:

$-\overset{O}{\overset{\|}{C}}-O-$, $-O-\overset{O}{\overset{\|}{C}}-$, $-\overset{O}{\overset{\|}{C}}-\overset{H}{\overset{|}{N}}-$, $-\overset{H}{\overset{|}{N}}-\overset{O}{\overset{\|}{C}}-$, $-O-$, $-O-\overset{O}{\overset{\|}{C}}-O-$, $-O-\overset{O}{\overset{\|}{C}}-\overset{H}{\overset{|}{N}}-$, and $-\overset{H}{\overset{|}{N}}-\overset{O}{\overset{\|}{C}}-O-$ and wherein at least one of said $Z^1$ or $Z^2$ groups is selected from the group consisting of ester, reverse ester, amide, and reverse amide; and X is an anion which makes the surfactant at least water-dispersible.

2. The compound of claim 1 wherein $Z^2$ is selected from the group consisting of ester, reverse ester, amide and reverse amide.

3. The compound of claim 2 wherein $Z^2$ is selected from the group consisting of ester and reverse ester.

4. The compound of claim 2 wherein $Z^2$ is selected from the group consisting of amide and reverse amide.

5. The compound of claim 2 wherein n is 4 and $R^2$ is hydrogen.

6. The compound of claim 2 wherein n is 2 and the $R^2$ groups are $CH_3$ and hydrogen respectively.

7. The compound of claim 2 wherein n is 2 and $R^2$ is hydrogen.

8. The compound of claim 7 wherein y is from 1 to 10.

9. The compound of claim 8 wherein $R^3$ is $C_8$ to $C_{18}$ alkyl.

10. The compound of claim 7 wherein a is 1 and $Z^1$ is $$-\overset{O}{\overset{\|}{C}}-.$$

11. The compound of claim 10 wherein t is 1 and $R^4$ is $C_2$ alkylene.

12. The compound of claim 7 wherein a is 0.

13. The compound of claim 12 wherein m is 2.

14. The compound of claim 13 wherein t is 1 and $R^4$ is methylene.

15. The compound of claim 14 wherein $Z^2$ is $$-\overset{O}{\overset{\|}{C}}-O-.$$

16. The compound of claim 15 wherein y is from 1 to 10.

17. The compound of claim 16 wherein $R^3$ is $C_8$ to $C_{18}$ alkyl.

18. The compound of claim 17 wherein $R^1$ is $CH_3$.

19. The compound of claim 18 wherein X is selected from the group consisting of halides, methyl sulfate, sulfate, and nitrate.

20. The compound of claim 19 wherein X is selected from the group consisting of chloride, bromide, iodide, sulfate and methyl sulfate.

21. The compound of claim 20 wherein y is 7.

22. The compound of claim 21 wherein $R^3$ is $C_{12}$ alkyl.

23. The compound of claim 7 wherein $Z^2$ is $$-O-\overset{O}{\overset{\|}{C}}-.$$

24. The compound of claim 23 wherein y is from 1 to 10.

25. The compound of claim 24 wherein $R^3$ is $C_8$ to $C_{18}$ alkyl.

26. A detergent composition containing from 0 to about 20% of phosphate materials, and having a pH in the laundry solution of not greater than about 11, comprising from about 5 to about 100% of a surfactant mixture consisting essentially of (a) a biodegradable nonionic surfactant having the formula $R(OC_2H_4)_nOH$ wherein R is a primary or secondary alkyl chain of from about 8 to about 22 carbon atoms and n is an average of from about 2 to about 12, having an HLB of from about 5 to about 17; and (b) the cationic surfactant of claim 1; said composition having a pH of at least about 6.5 in the aqueous laundry solution, and wherein the ratio of said nonionic to said cationic component is in the range of from about 1:1 to about 100:1.

27. The composition of claim 26 wherein, in the cationic surfactant, $Z^2$ is selected from the group consisting of ester, reverse ester, amide, and reverse amide.

28. The composition of claim 27 wherein the nonionic surfactant is selected from the group consisting of the condensation product of $C_{10}$ alcohol with 3 moles of ethylene oxide, the condensation product of coconut alcohol with 5 moles of ethylene oxide, the condensation product of $C_{12}$ alcohol with 5 moles of ethylene oxide, the condensation product of $C_{12-13}$ alcohol with 3 moles of ethylene oxide, and the same product which is stripped to remove substantially all lower ethoxylate and nonethoxylate fractins, the condensation product of $C_{12-13}$ alcohol with 6.5 moles of ethylene oxide, the condensation product of $C_{12-13}$ alcohol with 9 moles of ethylene oxide, the condensation product of $C_{14-15}$ alcohol with 3 moles of ethylene oxide, the condensation product of $C_{14-15}$ alcohol with 4 moles of ethylene oxide, the condensation product of $C_{14-15}$ alcohol with 7 moles of ethylene oxide, the condensation product of $C_{14-15}$ alcohol with 9 moles of ethylene oxide, and mixtures thereof.

29. The composition of claim 27 wherein, in the cationic surfactant, $Z^2$ is $$-\overset{O}{\overset{\|}{C}}-O-.$$

30. The composition of claim 29 wherein, in the cationic surfactant, n is equal to 2 and $R^2$ is hydrogen.

31. The composition of claim 30, wherein, in the cationic surfactant, a is 0 and m is equal to 2.

32. The composition of claim 31 wherein, in the cationic sufactant, $R^4$ is methylene and t is equal to 1.

33. The composition of claim 32 wherein, in the cationic surfactant, y is from 1 to 10.

34. The composition of claim 33 wherein, in the cationic surfactant, y is from 1 to 10.

35. The composition of claim 34 wherein, in the cationic surfactant, $R^1$ is $CH_3$.

36. The composition of claim 35 wherein, in the cationic surfactant, X is selected from the group consisting of chloride, bromide, iodide, methyl sulfate and sulfate.

37. The composition of claim 36 wherein, in the nonionic surfactant, R is an alkyl chain of from about 10 to about 18 carbon atoms.

38. The composition of claim 37 wherein, in the cationic surfactant, y is equal to 7.

39. The composition of claim 38 wherein, in the cationic surfactant, $R^3$ is $C_{12}$ alkyl.

40. The composition of claim 27 wherein the ratio of nonionic surfactant to cationic surfactant is from about 1:1 to 5:1, and the reduced cationic monomer concentration of the nonionic/cationic surfactant mixture is from about 0.005 to about 0.2.

41. The composition of claim 36 wherein the ratio of nonionic surfactant to cationic surfactant is from about 1:1 to 5:1, and the reduced cationic monomer concentration of the nonionic/cationic surfactant mixture is from about 0.005 to about 0.2.

42. The composition of claim 40 wherein the ratio of nonionic surfactant to cationic surfactant is from about 5:3 to 5:1.

43. The composition of claim 42 which is substantially free of phosphate, polyphosphate, silicate, and polycarboxylate builder anions, carboxymethylcellulose, and anionic surfactants.

44. The composition of claim 40 which is substantially free of oily hydrocarbon materials.

45. The composition of claim 27 wherein the ratio of nonionic surfactant to cationic surfactant is from 5.1:1 to about 100:1, the nonionic/cationic surfactant mixture has a cloud point of from about 0° to about 95° C., and the reduced cationic monomer concentration of the nonionic/cationic surfactant mixture is from about 0.002 to about 0.2.

46. The composition of claim 36 wherein the ratio of nonionic surfactant to cationic surfactant is from 5.1:1 to about 100:1, the nonionic/cationic surfactant mixture has a cloud point of from about 0° to about 95° C., and the reduced cationic monomer concentration of the nonionic/cationic surfactant mixture is from about 0.002 to about 0.2.

47. The composition of claim 45 which additionally contains from about 1 to about 60% of a detergency builder salt.

48. The composition of claim 45 wherein said composition forms separated phases when added to water having a temperature of about 45° C., at a concentration of from about 0.01 to about 0.3%.

49. The composition of claim 45 wherein the ratio of nonionic surfactant to cationic surfactant is from 5.1:1 to about 50:1.

50. The composition of claim 26 which has a pH of greater than about 7 in the aqueous laundry solution.

* * * * *